US008916135B2

(12) United States Patent
Boyes et al.

(10) Patent No.: US 8,916,135 B2
(45) Date of Patent: Dec. 23, 2014

(54) LANTHANIDE NANOPARTICLE CONJUGATES AND USES THEREOF

(75) Inventors: Stephen G. Boyes, Denver, CO (US); Misty D. Rowe, Golden, CO (US); Douglas H. Thamm, Fort Collins, CO (US); Susan L. Kraft, Fort Collins, CO (US)

(73) Assignees: Colorado School of Mines, Golden, CO (US); Colorado State University Research Foundation, Fort Collins, CO (US)

( * ) Notice: Subject to any disclaimer, the term of this patent is extended or adjusted under 35 U.S.C. 154(b) by 1451 days.

(21) Appl. No.: 12/197,061

(22) Filed: Aug. 22, 2008

(65) Prior Publication Data

US 2009/0060840 A1 Mar. 5, 2009

Related U.S. Application Data

(60) Provisional application No. 60/957,208, filed on Aug. 22, 2007.

(51) Int. Cl.
| | |
|---|---|
| *A61K 49/06* | (2006.01) |
| *C07F 5/00* | (2006.01) |
| *B82Y 5/00* | (2011.01) |
| *A61K 49/18* | (2006.01) |
| *A61B 5/055* | (2006.01) |

(52) U.S. Cl.
CPC ............ *C07F 5/003* (2013.01); *C07B 2200/11* (2013.01); *A61B 5/055* (2013.01); *B82Y 5/00* (2013.01); *A61K 49/1854* (2013.01)
USPC ..................................................... 424/9.322

(58) Field of Classification Search
None
See application file for complete search history.

(56) References Cited

U.S. PATENT DOCUMENTS

| | | | |
|---|---|---|---|
| 4,708,930 A | 11/1987 | Kortright et al. | |
| 4,743,543 A | 5/1988 | Kortright | |
| 4,892,935 A | 1/1990 | Yoshida et al. | |
| 4,914,021 A | 4/1990 | Toth et al. | |
| 4,918,164 A | 4/1990 | Hellstrom et al. | |
| 4,921,789 A | 5/1990 | Salem et al. | |
| 4,939,240 A | 7/1990 | Chu et al. | |
| 4,963,484 A | 10/1990 | Kufe | |
| 5,053,489 A | 10/1991 | Kufe | |
| 5,110,911 A | 5/1992 | Samuel et al. | |
| 5,270,163 A | 12/1993 | Gold et al. | |
| 5,475,096 A | 12/1995 | Gold et al. | |
| 5,512,443 A | 4/1996 | Schlom et al. | |
| 5,545,530 A | 8/1996 | Satomura et al. | |
| 5,693,763 A | 12/1997 | Codington et al. | |
| 5,808,005 A | 9/1998 | Codington et al. | |
| 5,855,866 A | 1/1999 | Thorpe et al. | |
| 5,892,019 A | 4/1999 | Schlom et al. | |
| 5,892,020 A | 4/1999 | Mezes et al. | |
| 7,102,024 B1 | 9/2006 | Schwartz et al. | |
| 7,402,690 B2 | 7/2008 | McCormick et al. | |
| 2002/0165179 A1 | 11/2002 | Baker, Jr. | |
| 2003/0199653 A1* | 10/2003 | McCormick et al. | ...... 526/219.6 |
| 2004/0052729 A1* | 3/2004 | Penades et al. | .............. 424/1.73 |
| 2005/0031692 A1 | 2/2005 | Beyerinck | |
| 2006/0233712 A1 | 10/2006 | Penades et al. | |
| 2007/0123670 A1 | 5/2007 | McCormick et al. | |
| 2009/0060839 A1 | 3/2009 | Boyes et al. | |
| 2009/0060840 A1 | 3/2009 | Boyes et al. | |
| 2012/0052006 A1 | 3/2012 | Boyes et al. | |

FOREIGN PATENT DOCUMENTS

| | | |
|---|---|---|
| WO | WO 93/11161 | 6/1993 |
| WO | WO 94/13804 | 6/1994 |
| WO | WO 97/38134 | 10/1997 |
| WO | WO 98/33941 | 8/1998 |
| WO | WO 99/07724 | 2/1999 |

OTHER PUBLICATIONS

Fustin CA, Colard C, Filali M, Guillet P, Duwez AS, Meier MA, Schubert US, Gohy JF. Tuning the hydrophilicity of gold nanoparticles templated in star block copolymers. 2006 Langmuir 22: 6690-6695. Published online Jun. 14, 2006.*
Adlish, et al., "Identification of a Putative Cell Receptor for Human Cytomegalovirus," *Virology*, 1990, vol. 176, pp. 337-345.
Ahrens, et al., "A model for MRI contrast enhancement using T1 agents," *Proc. Nat'l. Acad. Sci. U.S.A.*, 1998, vol. 95, pp. 8443-8448.
Aime, et al., "A $R_2R_1$ Ratiometric Procedure for a Concentration-Independent pH-Responsive, GD(III)-Based MRI Agent," *J. Am. Chem. Soc.*, 2006, vol. 128, pp. 11326-11327.
Allen, "Ligand-Targeted Therapeutics in Anticancer Therapy," *Nat. Rev. Cancer*, 2002, vol. 2, pp. 750-763 and 2 pages.
Bakalova, et al., "Multimodal Silica-Shelled Quantum Dots: Direct Intracellular Delivery, Photosensitization, Toxic, and Microcirculation Effects," *Bioconjugate Chem.*, 2008, vol. 19, pp. 1135-1142.
Binkley, et al., "RNA ligands to human nerve growth factor," *Nuc. Acids Res.*, 1995, vol. 23, No. 16, pp. 3198-3205.
Bird, et al., "Single-Chain Antigen-Binding Proteins," *Science*, 1988, vol. 242, pp. 423-426.
Bridot, et al., "Hybrid Gadolinium Oxide Nanoparticles: Multimodal Contrast Agents for in Vivo Imaging," *J. Am. Chem. Soc.*, 2007, vol. 129, pp. 5076-5084.
Burda, et al., "Chemistry and Properties of Nanocrystals of Different Shapes," *Chem. Rev.*, 2005, vol. 105, pp. 1025-1102.

(Continued)

*Primary Examiner* — Michael G Hartley
*Assistant Examiner* — Jennifer Lamberski
(74) *Attorney, Agent, or Firm* — Dorsey & Whitney LLP

(57) ABSTRACT

The present disclosure is directed generally to lanthanide nanoparticle conjugates, such as gadolinium nanoparticle conjugates, nanoparticle conjugates including polymers, conjugation to targeting agents and therapeutic agents, and their use in targeting, treating, and/or imaging disease states in a patient.

11 Claims, 18 Drawing Sheets

(56) References Cited

OTHER PUBLICATIONS

Caravan, et al., "Gadolinium(III) Chelates as MRI Contrast Agents: Structure, Dynammics and Application," *Chem. Rev.*, 1999, vol. 99, pp. 2293-2352.
Carel, et al., "Structural Requirements for C3d,g/Epstein-Barr Virus Receptor (CR2/CD21) Ligand Binding, Internalization, and Viral Infection," *J. Biol. Chem.*, 1990, vol. 265, No. 21, pp. 12293-12299.
Carter, "Potent antibody therapeutics by design," *Nature Reviews Immunology*, 2006, vol. 6, pp. 343-357.
Cheon, et al., "Synergistically Integrated Nanoparticles as Multimodal Probes for Nanobiotechnology," *Accounts of Chem. Res.*, published online at www.pubs.acs.org/acr on Aug. 13, 2008, pp. 1630-1640.
Co, et al., "Isolation and biochemical characterization of the mammalian reovirus type 3 cell-surface receptor," *Proc. Nat'l. Acad. Sci. U.S.A*, 1985, vol. 82, pp. 1494-1498.
Dalgleish, et al., "The CD4 (T4) antigen is an essential component of the receptor for the AIDS retrovirus," *Nature*, 1984, vol. 312, pp. 763-766.
Daniel, et al., "Gold Nanoparticles: Assembly, Supramolecular Chemistry, Quantum-Size-Related Properties, and Applications toward Biology, Catalysis, and Nanotechnology," *Chem. Rev.*, 2004, vol. 104, No. 1, pp. 293-346.
Eppstein, et al., "Epidermal growth factor receptor occupancy inhibits vaccinia virus infection," *Nature*, 1985, vol. 318, pp. 663-665.
Ferrari, "Cancer Nanotechnology: Opportunities and Challenges," *Nature Rev. Cancer*, 2005, vol. 5, pp. 161-171.
Frullano, et al., "Multimodal MRI Contrast Agents," *J. Biol. Inorg. Chem.*, 2007, vol. 12, pp. 939-949.
Fu, et al., "Cascade Polymeric MRI Contrast Media Derived from Poly(ethylene glycol) Cores: Initial Syntheses and Characterizations,"*Biomacromolecules*, 2007, vol. 8, pp. 1519-1529.
Hanisch, et al., "Structural Studies on Oncofetal Carbohydrate Antigens (CA 19-9, CA 50, and CA 125) Carried by O-Linked Sialyloligosaccharides on Human Amniotic Mucins," *Carbohydr. Res.*, 1988, vol. 178, pp. 29-47.
Harlow, et al., "Using Antibodies: A Laboratory Manual," 1999, Cold Spring Harbor Laboratory Press, 5 pages.
Hifumi, et al., "Gadolinium-Based Hybrid Nanoparticles as a Positive MR Contrast Agent," *J. Am. Chem. Soc.*, 2006, vol. 128, No. 47, pp. 15090-15091.
High, et al. "Gadolinium is detectable within the tissue of patients with nephrogenic systemic fibrosis," *J. Am. Acad. Dermatol.*, 2007, vol. 56, pp. 21-26.
Hinoda, et al., "Immunochemical Characterization of Adenocarcinoma-Associated Antigen YH206," *Int'l Cancer Journal*, 1988, vol. 42, pp. 653-658.
Holliger, et al., ""Diabodies": Small bivalent and bispecific antibody fragments," *Proc. Nat'l. Acad. Sci. U.S.A.*, 1993, vol. 90, pp. 6444-6448.
Holliger, et al., "Engineered antibody fragments and the rise of single domains," *Nature Biotechnology*, 2005, vol. 23, No. 9, pp. 1126-1136.
Huang, et al., "Cancer Cell Imaging and Photothermal Therapy in the Near-Infrared Region by Using Gold Nanorods," *J. Am. Chem. Soc.*, 2006, vol. 128, pp. 2115-2120.
Huston, et al., "Protein engineering of antibody binding sites: Recovery of specific activity in an anti-digoxin single-chain Fv analogue produced in *Escherichia coli,*" *Proc. Nat'l. Acad. Sci. U.S.A.*, 1988, vol. 85, pp. 5879-5883.
Ishida, et al., "Related Glycoprotiens from Normal Secretory and Malignant Brest Cells: Purification and Intitial Comparative Characterizations," *Tumor Biol.*, 1989, vol. 10, pp. 12-22 and 1 page.
Jellinek, et al., "Inhibition of Receptor Binding by High-Affinity RNA Ligands to Vascular Endothelial Growth Factor," *Biochem.*, 1994, vol. 33, No. 34, pp. 10450-10456.
Kaner, et al., "Fibroblast Growth Factor Receptor Is a Portal of Cellular Entry for Herpes Simplex Virus Type 1," *Science*, 1990, vol. 248, pp. 1410-1413.
Kim, et al., "Antibiofouling Polymer-Coated Gold Nanoparticles as a Contrast Agent for in Vivo X-ray Computed Tomography Imaging," *J. Am. Chem. Soc.*, 2007, vol. 129, pp. 7661-7665.
Kjeldsen, et al., "Preparation and Characterization of Monoclonal Antibodies Directed to the Tumor-associated O-linked Sailosyl-2-6 a-N-Acetylgalactosaminyl (Sialosyl-Tn) Epitope," *Cancer Research*, 1988, vol. 48, pp. 2214-2220.
Klatzmann, et al., "T-lymphocyte T4 molecule behaves as the receptor for human retrovirus LAV," *Nature*, 1984, vol. 312, pp. 767-768.
Krah, "Characterization of Octyl Glucoside-Solubilized Cell Membrane Receptors for Binding Measles Virus," *Virology*, 1989, vol. 172, pp. 386-390.
Kukowska-Latallo, et al., "Nanoparticle Targeting of Anticancer Drug Improves Therapeutic Response in Animal Model of Human Epithelial Cancer," *Cancer Research*, 2005, vol. 65, pp. 5317-5324.
Lan, et al., "Isolation and Properties of a Human Pancreatic Adenocarcinoma-associated Antigen, DU-PAN-2," *Cancer Res.*, 1985, vol. 45, pp. 305-310.
Lentz, et al., "Is the Acetylcholine Receptor a Rabies Virus Receptor'?," *Science*, 1982, vol. 215, pp. 182-184.
Lu et al., "Mesoporous Silica Nanoparticles as a Delivery System for Hydrophobic Anticancer Drugs," *Small*, 2007, vol. 3, No. 8, pp. 1341-1346.
Marlin, et al., "A soluble form of intercellular adhesion molecule-1 inhibits rhinovirus infection," *Nature*, 1990, vol. 344, pp. 70-72.
Mendelsohn, et al., "Cellular Receptor for Poliovirus: Molecular Cloning, Nucleotide Sequence, and Expression of a New Member of the Immunoglobulin Superfamily," *Cell*, 1989, vol. 56, pp. 855-865.
Murphy, et al., "Anisotropic Metal Nanoparticles: Synthesis, Assembly, and Optical Applications," *J. Phys. Chem. B*, 2005, vol. 109, pp. 13857-13870.
Nasongkla, et al., "Multifunctional Polymeric Micelles as Cancer-Targeted, MRI-Ultrasensitive Drug Delivery Systems," *Nano Letters*, 2006, vol. 6, No. 11, pp. 2427-2430.
Niidome, et al., "PEG-modified gold nanorods with a stealth character for in vivo applications," *J. Controlled Release*, 2006, vol. 114, pp. 343-347.
Odian, *Principles of Polymerization*, 4th Edition, Wiley-Interscience, 2004, 19 pages.
Oyewumi, "Comparison of cell uptake, biodistribution and tumor retention of folate-coated and PEG-coated gadolinium nanoparticles in tumor-bearing mice," *Journal of Controlled Release*, 2004, vol. 95, pp. 613-626.
Park, "Nanotechnology: What it can do for drug delivery," *J. Controlled Release*, 2007, vol. 120, pp. 1-3.
Park, "Tumor-directed Targeting of Liposomes," *Biosci. Rep.*, 2002, vol. 22, No. 2, pp. 267-281.
Perez-Juste, et al., "Gold-nanorods: Synthesis, characterization and applications," *Coordination Chemistry Reviews*, 2005, vol. 249, pp. 1870-1901.
*Remington: Practice of the Science and Pharmacy*, 19th Edition, Alfonso R. Gennaro, ed., 1995, Chapter 83, pp. 1447-1675 and 3 cover pages.
Rieter, et al. , "Nanoscale Metal-Organic Frameworks as Potential Multimodal Contrast Enhancing Agents," *J. Am Chem. Soc.*, 2006, vol. 128, pp. 9024-9025.
Rowe, et al ., Synthesis of Surface-Initiated Stimuli-Responsive Diblock Copolymer Brushes Utilizing a Combination of ATRP and RAFT Polymerization Techniques, *Macromolecules*, 2008, vol. 41, No. 12, pp. 4147-4157.
Rowe-Konopacki, et al., "Synthesis of Surface Initiated Diblock Copolymer Brushes from Flat Silicon Substrates Utilizing the RAFT Polymerization Technique," *Macromolecules*, 2007, vol. 40, No. 4, pp. 879-888.
Ruff, et al., "CD4 receptor binding peptides that block HIV infectivity cause human monocyte chemotaxis," *FEBS Letters*, 1987, vol. 211, No. 1, pp. 17-22.
Sacerdote, et al., "Vasoactive Intestinal Peptide 1-12: A Ligand for the CD4 (T4)/Human Immunodeficiency Virus Receptor," *J. Neuroscience Research*, 1987, vol. 18, pp. 102-107 and 1 page.
Sau, et al., "Seeded High Yield Synthesis of Short Au Nanorods in Aqueous Solution," *Langmuir*, 2004, vol. 20, No. 15, pp. 6414-6420.

(56) References Cited

OTHER PUBLICATIONS

Sebra, "Surface Grafted Antibodies: Controlled Architecture Permits Enhanced Antigen Detection," *Langmuir*, 2005, vol. 21, No. 24, pp. 10907-10911.
Service, "Nanotechnology Takes Aim at Cancer," *Science*, 2005, vol. 310, pp. 1132-1134.
Shepley, et al., "Monoclonal antibody identification of a 100-kDa membrane protein in HeLa cells and human spinal cord involved in poliovirus attachment," *Proc. Nat'l. Acad. Sci. U.S.A.*, 1988, vol. 85, pp. 7743-7747.
Slowing, et al., "Mesoporous Silica Nanoparticles for Intracellular Delivery of Membrane-Impermeable Proteins," *J. Am. Chem. Soc.*, 2007, vol. 129, pp. 8845-8849.
Solberg, et al., "Adsorption of DNA into Mesoporous Silica," *J. Phys. Chem. B*, 2006, vol. 110, No. 31, pp. 15261-15268.
Springer, et al., "Blood Group Tn-Active Macromolecules from Human Carcinomas and Erythrocytes: Characterization of and Specific Reactivity with Mono-and Poly-Clonal Anti-Tn Antibodies Induced by Various Immunogens," *Carbohydr. Res.*, 1988, vol. 178, pp. 271-292.
Su, et al., "Nanoshell Magnetic Resonance Imaging Contrast Agents," *J. Am. Chem. Soc.*, 2007, vol. 129, pp. 2139-2146.
Tjandra, et al., "Application of mammary serum antigen assay in the management of breast cancer: a preliminary report," *Br. J. Surg.*, 1988, vol. 75, No. 8, pp. 811-817.
Tomlinson, et al., "Methods for Generating Multivalent and Bispecific Antibody Fragments," *Methods Enzymol.*, 2000, vol. 326, pp. 461-479.
Tuerk, et al., "In vitro evolution of functional nucleic acids: high-affinity RNA ligands of HIV-1 proteins," *Gene.*, 1993, vol. 137, pp. 33-39.
Ward, et al., "Binding activities of a repertoire of single immunoglobulin variable domains secreted from *Escherichia coli*," *Nature*, 1989, vol. 341, pp. 544-546.
Weis, et al., "Sructure of the influenza virus haemagglutinin complexed with its receptor, sialic acid," *Nature*, 1988, vol. 333, pp. 426-431.
White, et al., "Viral Receptors of the Immunoglobulin Superfamily," *Cell*, 1989, vol. 56, pp. 725-728.
Wyrick, et al., "Entry of Genital *Chlamydia trachomatis* into Polarized Human Epithelial Cells," *Infect. and Immunity*, 1989, vol. 57, No. 8, pp. 2378-2389.
Yanjarappa, "Synthesis of Copolymers Containing an Active Ester of Methacrylic Acid by RAFT: Controlled Molecular Weight Scaffolds for Biofunctionalization," *Biomacromolecules*, 2006, vol. 7, No. 5, pp. 1665-1670.
Zola, "Monoclonal Antibodies: Preparation and use of monoclonal antibodies and engineered antibody derivatives," 2000, Springer Verlag, 1st Edition.
"US Final Office Action", US Final Office Action dated Jun. 20, 2014, U.S. Appl. No. 13/202,311, 20 pages.
International Search Report and Written Opinion for US Application No. PCT/US2010/024450, dated Jul. 24, 2010, 8 pages.
Alric et al., "Gadoliniuim Chelate Coated Gold Nanoparticles as Contrast Agents for Both X-ray Computed Tomography and Magnetic Resonance Imating", J. Am. Chem. Soc., 130, 2008, 5908-5915.
Chang et al., "Preparation of Fluorescent Magnetic Nanodiamonds and Cellular Imaging", J. Am. Chem. Soc., 2008, 130 (46), 1022/2008, 15476-15481.
Lowe et al., "Facile preparation of transition metal nanoparticles stabilized by well-defined (Co)polymers synthesized via aqueous reversible addition-fragmentation chain transfer polymerization", J. Am. Chem. Soc. (2002), 124, 11562-11563.
Martin et al., "Nanomaterials in Analytical Chemistry", Analytical Chem. News & Features, May 1, 1998, 322-327, 12 pages.
PCT International Search Report dated Dec. 19, 2008, PCT Application No. PCT/US2008/74065, filed Aug. 22, 2008, 3 pages.
US Amendment and Response to Non-Final Office Action dated Nov. 21, 2011, U.S. Appl. No. 12/197,044, 11 pages.
US Notice of Appeal dated Aug. 27, 2012, U.S. Appl. No. 12/197,044, 1 page.
US Notice of Final Rejection dated Jan. 4, 2012, U.S. Appl. No. 12/197,044, 6 pages.
US Notice of Non-Final Rejection dated May 19, 2011, U.S. Appl. No. 12/197,044 7 pages.
US Pre-Appeal Brief Request for Review and Arguments dated May 3, 2012, U.S. Appl. No. 12/197,044, 5 pages.
US Request for Continued Examination dated May 3, 2012, U.S. Appl. No. 12/197,044, 3 pages.
US Response to Election/Restriction dated Mar. 4, 2011, U.S. Appl. No. 12/197,044, 7 pages.
US Restriction/Election Requirement dated Feb. 4, 2011, U.S. Appl. No. 12/197,044 8 pages.
US Non-Final Rejection dated Dec. 4, 2013, U.S. Appl. No. 13/202,311, 18 pages.
US Notice regarding Non-Compliant or Non-Responsive Amendment dated Jul. 5, 2013, U.S. Appl. No. 13/202,311, 2 pages.
US Response to Election/Restriction dated Nov. 19, 2012, U.S. Appl. No. 13/202,311, 12 pages.
US Supplemental Response or Amendment to Notice regarding Non-Compliant or Non-Responsive Amendment dated Jul. 26, 2013, U.S. Appl. No. 13/202,311, 9 pages.
US Restriction/Election Requirement dated Sep. 9, 2012, U.S. Appl. No. 13/202,311, 12 pages.
Rieter et al., "Surface Modification and Functionalization of Nanoscale Metal-Organic Frameworks for Controlled Release and Luminescence Sensing", J. Am. Chem. Soc., May 17, 2007, 2 pages.
Seevinck et al., "Factors Affecting the Sensitivity and Detection Limits of MRI, CT, and SPECT for Multimodal Diagnostic and Therapeutic Agents", Anti-Cancer Agent in Medicinal Chemistry (Formerly Current Medicinal Chemistry—Anti-Cancer Agents), vol. 7, No. 3, May 2007, pp. 317-334(18).
Sumerlin et al., "Modification of gold surfaces with water-soluble (Co)polymers prepared via aqueous reversible addition—fragmentation chain transfer (RAFT) polymerization", Langmuir (2003), 19, 5559-5562.
US Response to Non-Final Office Action dated Jun. 4, 2014, U.S. Appl. No. 13/202,311, 15 pages.
Non-Final Office Action dated Sep. 9, 2014 issued for U.S. Appl. No. 12/197,044, 13 pages.

\* cited by examiner

LANTHANIDE NANOPARTICLE CONJUGATES AND USES THEREOF

CROSS REFERENCE TO RELATED APPLICATIONS

This application claims the benefit of priority under 35 U.S.C. 119(e) of U.S. Provisional Application No. 60/957,208 entitled Gadolinium and Gold Nanoparticle Conjugates and Uses Thereof, filed Aug. 22, 2007, which is hereby incorporated by reference. This application is also related to copending application Ser. No. 12/197,044 entitled Gold Nanoparticle Conjugates and Uses Thereof, filed Aug. 22, 2008, which is hereby incorporated by reference.

FIELD

The disclosure generally relates to formation of polymers grafted to or polymerized from the surface of lanthanide, e.g. gadolinium, nanoparticles. The polymers are functionalized to include therapeutic agents and targeting agents at their surface, thereby allowing both imaging and targeting therapeutic compounds to specific cells in a patient.

BACKGROUND

One of the most important areas of research in the general field of nanotechnology is in the development of nanomedicines, which refers to highly specific medical intervention at the molecular scale for diagnosis, prevention, and treatment of diseases. Park, K. J. Controlled Release 2007, 120, 1-3, incorporated by reference in its entirety. The importance of this area is highlighted by the recent establishment of the National Institutes of Health (NIH) Nanomedicine Roadmap Initiative, where over $1 billion has been committed in an attempt to revolutionize the areas of therapeutics and diagnostics through the development and application of nanotechnology and nanodevices. One of the most exciting areas of nanomedicine is the development of nanodevices for theragnostics, which refers to a combination of diagnostics and therapeutics for tailored treatment of diseases. The synthesis of nanodevices that incorporate therapeutic agents, molecular targeting, and diagnostic imaging capabilities have been described as the next generation nanomedicines and have the potential to dramatically improve the therapeutic outcome of drug therapy (e.g. Nasongkla, N. et al. *Nano Lett.* 2006, 6, 2427-2430) and lead to the development of personalized medicine, where the device may be tailored for treatment of individual patients on the basis of their genetic profiles. While there is almost unanimous agreement in the scientific community that these next generation nanomedicines will provide clinically important theragnosis devices, they have yet to be clinically realized.

One of the primary reasons for this is the poor design and manufacturing techniques of the current nanodevices. The main problems with the current manufacturing techniques include low drug and/or targeting moiety loading capacity, low loading efficiencies, and poor ability to control the size distribution, surface interactions, and in vivo performance of the devices. See, e.g., Park, K. J. *Controlled Release* 2007, 120, 1-3. In conjunction to these manufacturing problems, current design issues center around a lack of flexibility in the construct which may limit the type and quantity of drug and/or targeting agent that may be incorporated, provide little or no control over spatial orientation and architecture of the nanoparticle, and have stability issues with the particle structure or with the drug and/or targeting agent incorporated in the particle.

Recently polymer-based nanodevices have received much attention and many believe that they are the most promising for clinical translation. See, e.g., Bridot, J.-L. et al. *J. Am. Chem. Soc.* 2007. Examples of polymer-based theragnostic nanodevices include dendrimers, polymeric micelles, and polymer-based core-shell nanoparticles. While dendrimers have proven to be effective for drug delivery or targeted molecular imaging, it is difficult to control the loading capacity and efficiency of the drug, imaging and/or targeting agent. Polymeric micelles use a hydrophobic core to carry therapeutics and imaging agents, while targeting agents are attached to the hydrophilic corona. However, micelle structures are susceptible to instabilities due to changes in the surrounding in vivo environment and have limited control of loading capacity. Polymer-based core-shell nanoparticles offer improved stability over polymer micelles; however, it is often difficult to release therapeutic agents contained within the core of the structure which tends to inhibit their therapeutic value.

One area that has reached significant commercial application is the use of targeted drug delivery. This represents an extremely diverse area due to the large number of diseases that potentially benefit from targeted delivery. As the current focus of research into the invention has been on the targeted imaging and treatment of cancer, this discussion will focus on competitive products in the areas of cancer therapy and diagnosis. However, the inherent flexibility of the invention allows for its potential use in any disease that would benefit from theragnosis.

Current magnetic resonance imaging (MRI) techniques employ gadolinium as a contrast agent. Gadolinium metal is highly toxic to cells. For MRI application, this toxicity has been overcome by utilizing chelates to increase stability and compatibility of the metal ion. However, concerns have arisen with current in vivo use of gadolinium chelates due to non-specific cellular uptake and accumulation within healthy cells. Several groups have attempted to overcome these issues by using cascade polymers and dendrimers, however size distribution and spatial loading is poor. Gadolinium oxide nanoparticles have proven to be interesting because of their effectiveness as MRI contrast agents. Modification of these particles with polymers shows promise as a means to compatiblize the surface of gadolinium nanoparticles for in vivo imaging and to affix moieties that will potentially allow for targeting and treatment of cancer cells through control of nanoparticle-cellular surface interactions. Though recent advances have been made in the synthesis and modification of metal nanoparticles, the modification and characterization of gadolinium frameworks, such as gadolinium oxide nanoparticles, is still limited.

Against this backdrop, the present disclosure has been developed.

SUMMARY

The present disclosure is directed generally to lanthanide nanoparticle conjugates, such as gadolinium nanoparticle conjugates, nanoparticle conjugates including polymers, conjugation to targeting agents and therapeutic agents, and their use in targeting, treating, and/or imaging disease states in a patient. In certain embodiments, the gadolinium nanoparticle conjugates are multifunctional polymeric systems. Biocompatible polymer backbones that can be conjugated to imaging agents, targeting agents, and therapeutic agents are produced. Post-polymerization modification of the polymer backbone allows attachment of targeting agents or therapeutic agents to a functional group. The resulting gadolinium nanoparticle conjugates provide the ability to target, treat, and image diseased cells.

In one aspect, gadolinium nanoparticle conjugates are provided. The conjugate includes a gadolinium nanoparticle and a polymer or polymer precursor containing a functional group attached to the nanoparticle. As used herein, polymer precursors include components of polymers, such as monomers, dimers, etc., or initiators bonded to the gadolinium nanoparticle prior to polymerization. In various aspects, the functional group is selected from the group consisting of thiolates, thioethers, thioesters, carboxylates, amines, amides, halides, phosphonates, phosphonate esters, phosphinates, sulphonates, sulphates, porphyrins, nitrates, pyridine, pyridyl based compounds, nitrogen containing ligands, oxygen containing ligands, and sulfur containing ligands. In certain embodiments, the polymer, polymer precursor or initiator can be grafted onto the gadolinium nanoparticle by a covalent or non-covalent bond between a functional group and nanoparticle. In certain embodiments, the functional group is a single thiol group and vacant orbital present on the gadolinium (III) cation. In further aspects, the gadolinium nanoparticle conjugate can have the chemical structure according to Formula (I):

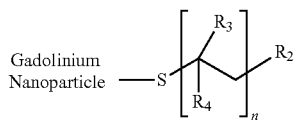

I wherein n is an integer;

$R_1$, $R_2$, $R_3$, and $R_4$ are each independently selected from hydrogen, alkyl, substituted alkyl, alkoxy, substituted alkoxy, acyl, substituted acyl, acylamino, substituted acylamino, alkylamino, substituted alkylamino, alkylsulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, aryloxycarbonyl, substituted aryloxycarbonyl, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroiryl, heteroarylalkyl, substituted heteroarylalkyl, heteroalkyloxy, substituted heteroalkyloxy, heteroaryloxy and substituted heteroaryloxy.

In other embodiments, $R_2$ is includes a functional group selected from thiolates, thioethers, thioesters, carboxylates, amines, amides, halides, phosphonates, phosphonate esters, phosphinates, sulphonates, sulphates, porphyrins, nitrates, pyridine, pyridyl based compounds, nitrogen containing ligands, oxygen containing ligands, and sulfur containing ligands.

The gadolinium nanoparticle conjugate can further include a functional group. In certain variations, the functional group can be selected from carboxylic acids and carboxylic acid salt derivatives, acid halides, sulfonic acids and sulfonic acid salts, anhydride derivatives, hydroxyl derivatives, amine and amide derivatives, silane derivations, phosphate derivatives, nitro derivatives, succinimide and sulfo-containing succinimide derivatives, halide derivatives, alkene derivatives, morpholine derivatives, cyano derivatives, epoxide derivatives, ester derivatives, carbazole derivatives, azide derivatives, alkyne derivatives, acid containing sugar derivatives, glycerol analogue derivatives, maleimide derivatives, protected acids and alcohols, and acid halide derivatives.

In other variations, the gadolinium nanoparticle conjugate includes a therapeutic agent. In further variations, the gadolinium nanoparticle further includes a targeting agent. Both the therapeutic agent and targeting agent are bonded to the polymer, optionally via a covalent linker or functional group.

In another aspect, the disclosure is directed to a pharmaceutical composition comprising the gadolinium nanoparticle conjugate as described herein, and a pharmaceutically acceptable carrier.

In a further aspect, the disclosure is directed to methods of making gadolinium nanoparticle conjugates. A gadolinium nanoparticle having a suitable initiator is contacted with a dithioester, xanthate, or dithiocarbamate of formula (II) or a trithiocarbonate of formula (III):

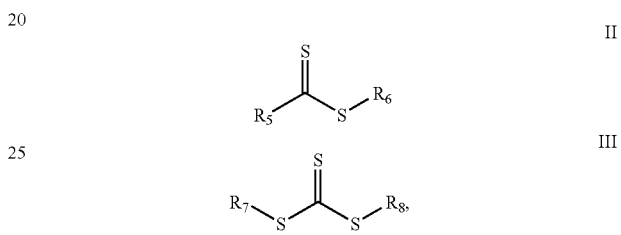

wherein $R_5$, $R_6$, $R_7$, and $R_8$ are each independently selected from hydrogen, alkyl, substituted alkyl, alkoxy, substituted alkoxy, acyl, substituted acyl, acylamino, substituted acylamino, alkylamino, substituted alkylamino, alkylsulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, aryloxycarbonyl, substituted aryloxycarbonyl, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy and substituted heteroaryloxy.

In other embodiments, $R_6$ and $R_8$ are each independently selected from a dithioester, xanthate, dithiocarbamate and trithiocarbonate to form a gadolinium nanoparticle conjugate with the compounds of formulae (II) or (III). Alternatively, the polymer or polymer precursor can be treated with a reducing agent to the compound of formulae (II) or (III) before contacting said gadolinium nanoparticle with said compound of formula (II) or (III).

In further aspects, the disclosure is directed to a method of treating a disease or disorder by administering a gadolinium nanoparticle conjugate to a patient in need of treatment of said disease or disorder. In various embodiments, the targeting agent localizes the nanoparticle conjugate to the site of the disease or disorder. The therapeutic agent treats said disease or disorder. The method can be further combined with imaging the gadolinium nanoparticle conjugate at the disease location.

BRIEF DESCRIPTION OF THE DRAWINGS

The disclosed Figures are exemplary, and are not intended to be limiting of the claims.

DETAILED DESCRIPTION

Figure 1A:
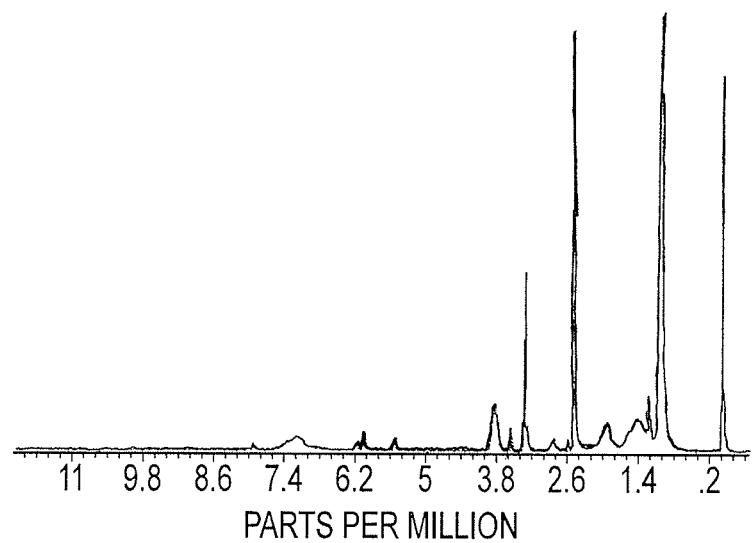
FIG. 1a depicts a ¹H NMR spectrum of PNIPAM-co-PNAOS-co-PFMA copolymer.

There has been an increasing focus on the development of multifunctional nanomedicines for improvement in the remedial results of drug treatment for cancer patients. See, e.g., Kukowska-Latallo, et al., Cancer Res. 2005, 65, 5317-5324. Sau, T. K. et al., Langmuir 2004, 20, 6414-6420; and Niidome, T. et al., Journal of Controlled Release 2006, 114, 343-347. Multifunctional nanomedicines incorporate diagnostic imaging capabilities, targeting through biomolecular recognition, and a therapeutic agent for treatment of a specific disease, providing a "one dose" approach of overcoming downfalls of conventional treatment and imaging techniques.

The present disclosure relates to preparation of lanthanide, and specifically gadolinium, nanoparticle conjugates comprising a gadolinium nanoparticle grafted onto a polymer or polymer precursor comprising a functional group. The functional group serves as the point of attachment to the gadolinium nanoparticle. Thus, molecules are specifically bonded to gadolinium nanoparticles by a specific functional group.

DEFINITIONS

A dash ("-") that is not between two letters or symbols is used to indicate a point of attachment for a moiety or substituent. For example, —CONH₂ is attached through the carbon atom.

"Grafting" or "grafted onto" as used herein refers to attaching a polymer, polymer precursor or small molecule to the surface of a nanoparticle via a single functional group. Grafting includes both covalent and non-covalent binding, as well as, but not limited to, delocalized bond formation between one or more atoms of the nanoparticle and one or more atoms of the functional group, ionic bonding, hydrogen bonding, dipole-dipole bonding, and van der Waals forces. Formation of exemplary bonds are depicted in Schemes 2 and 3 described herein. The terms "grafting" and "grafting onto" include methods conventionally referred to as grafting from and grafting to.

"Covalent grafting" as used herein refers to attaching a polymer, polymer precursor, or small molecule by one or more covalent bonds from a functional group to the surface of a nanoparticle or by a delocalized bond complex, such as a delocalized bond complex.

"Alkyl" by itself or as part of another substituent refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In some embodiments, an alkyl group comprises from 1 to 20 carbon atoms. In other embodiments, an alkyl group comprises from 1 to 10 carbon atoms. In still other embodiments, an alkyl group comprises from 1 to 6 carbon atoms.

"Alkanyl" by itself or as part of another substituent refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" by itself or as part of another substituent refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical —C(O)R$^{30}$, where R$^{30}$ is hydrogen, alkyl, cycloalkyl, cycloheteroalkyl, aryl, arylalkyl, heteroalkyl, heteroaryl or heteroarylalkyl as defined herein. Representative examples include, but are not limited to formyl, acetyl, cyclohexylcarbonyl, cyclohexylmethylcarbonyl, benzoyl, benzylcarbonyl and the like.

"Acylamino" by itself or as part of another substituent refers to a radical —NR$^{31}$C(O)R$^{32}$, where R$^{31}$ and R$^{32}$ are independently hydrogen, alkyl, cycloalkyl, cycloheteroalkyl, aryl, arylalkyl, heteroalkyl, heteroaryl or heteroarylalkyl as defined herein. Representative examples include, but are not limited to formamido, acetamido and benzamido.

"Acyloxy" by itself or as part of another substituent refers to a radical —OC(O)R$^{33}$, where R$^{33}$ is alkyl, cycloalkyl, cycloheteroalkyl, aryl, arylalkyl, heteroalkyl, heteroaryl or heteroarylalkyl as defined herein. Representative examples include, but are not limited to acetoxy, isobutyroyloxy, benzoyloxy, phenylacetoxy and the like.

"Alkoxy" by itself or as part of another substituent refers to a radical —OR$^{34}$ where R$^{34}$ represents an alkyl or cycloalkyl group as defined herein. Representative examples include, but are not limited to, methoxy, ethoxy, propoxy, butoxy, cyclohexyloxy and the like.

"Alkylamino" means a radical —NHR where R represents an alkyl or cycloalkyl group as defined herein. Representative examples include, but are not limited to, methylamino, ethylamino, 1-methylethylamino, cyclohexyl amino and the like.

"Alkoxycarbonyl" by itself or as part of another substituent refers to a radical —C(O)—OR$^{35}$ where R$^{35}$ represents an alkyl or cycloalkyl group as defined herein. Representative examples include, but are not limited to, methoxycarbonyl, ethoxycarbonyl, propoxycarbonyl, butoxycarbonyl, cyclohexyloxycarbonyl and the like.

"Alkoxycarbonylamino" by itself or as part of another substituent refers to a radical —NR$^{36}$C(O)—OR$^{37}$ where R$^{36}$ represents an alkyl or cycloalkyl group and R$^{37}$ is alkyl, cycloalkyl, cycloheteroalkyl, aryl, arylalkyl, heteroalkyl, heteroaryl, heteroarylalkyl as defined herein. Representative examples include, but are not limited to, methoxycarbonylamino, tert-butoxycarbonylamino and benzyloxycarbonylamino.

"Alkoxycarbonyloxy" by itself or as part of another substituent refers to a radical —OC(O)—OR$^{38}$ where R$^{33}$ represents an alkyl or cycloalkyl group as defined herein. Representative examples include, but are not limited to, methoxycarbonyloxy, ethoxycarbonyloxy and cyclohexyloxycarbonyloxy.

"Alkylsulfinyl" refers to a radical —S(O)R where R is an alkyl or cycloalkyl group as defined herein. Representative examples include, but are not limited to, methylsulfinyl, ethylsulfinyl, propylsulfinyl, butylsulfinyl and the like.

"Alkylsulfonyl" refers to a radical —S(O)$_2$R where R is an alkyl or cycloalkyl group as defined herein. Representative examples include, but are not limited to, methylsulfonyl, ethylsulfonyl, propylsulfonyl, butylsulfonyl and the like.

"Alkylthio" refers to a radical —SR where R is an alkyl or cycloalkyl group as defined herein that may be optionally substituted as defined herein. Representative examples include, but are not limited to methylthio, ethylthio, propylthio, butylthio and the like.

"Aryl" by itself or as part of another substituent refers to a monovalent aromatic hydrocarbon radical derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group is from 6 to 20 carbon atoms. In other embodiments, an aryl group is from 6 to 12 carbon atoms.

"Arylalkyl" by itself or as part of another substituent refers to an acyclic alkyl radical in which one of the hydrogen atoms bonded to a carbon atom, typically a terminal or $sp^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In some embodiments, an arylalkyl group is ($C_6$-$C_{30}$) arylalkyl, e.g., the alkanyl, alkenyl or alkynyl moiety of the arylalkyl group is ($C_1$-$C_{10}$) and the aryl moiety is ($C_6$-$C_{20}$). In other embodiments, an arylalkyl group is ($C_6$-$C_{20}$) arylalkyl, e.g., the alkanyl, alkenyl or alkynyl moiety of the arylalkyl group is ($C_1$-$C_8$) and the aryl moiety is ($C_6$-$C_{12}$).

"Aryloxycarbonyl" refers to a radical —C(O)—O-aryl where aryl is as defined herein.

"Aryloxy" refers to a radical —C—O-aryl where aryl is as defined herein.

"Carbamoyl" by itself or as part of another substituent refers to the radical —C(O)NR$^{39}$R$^{40}$ where R$^{39}$ and R$^{40}$ are independently hydrogen, alkyl, cycloalkyl or aryl as defined herein.

"Carbamoyloxy" by itself or as part of another substituent refers to the radical —OC(O)NR$^{41}$R$^{42}$ where R$^{41}$ and R$^{42}$ are independently hydrogen, alkyl, cycloalkyl or aryl as defined herein.

"Compounds" of as defined by a chemical formula as disclosed herein include any specific compounds within the formula. Compounds may be identified either by their chemical structure and/or chemical name. When the chemical structure and chemical name conflict, the chemical structure is determinative of the identity of the compound. The compounds described herein may comprise one or more chiral centers and/or double bonds and therefore may exist as stereoisomers such as double-bond isomers (i.e., geometric isomers), enantiomers, or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled artisan.

Compounds include, but are not limited to, optical isomers of compounds, racemates thereof, and other mixtures thereof. In such embodiments, the single enantiomers or diastereomers, i.e., optically active forms, can be obtained by asymmetric synthesis or by resolution of the racemates. Resolution of the racemates may be accomplished, for example, by conventional methods such as crystallization in the presence of a resolving agent, or chromatography, using, for example a chiral high-pressure liquid chromatography (HPLC) column. In addition, compounds can include Z- and E-forms (or cis- and trans-forms) of compounds with double bonds.

Compounds may also include isotopically labeled compounds where one or more atoms have an atomic mass different from the atomic mass conventionally found in nature. Examples of isotopes that may be incorporated into the compounds disclosed herein include, but are not limited to, $^2$H, $^3$H, $^{11}$C, $^{13}$C, $^{14}$C, $^{15}$N, $^{18}$O, $^{17}$O, etc. Compounds may exist in unsolvated forms as well as solvated forms, including hydrated forms and as N-oxides. In general, compounds as referred to herein may be free acid, hydrated, solvated, or N-oxides of a Formula. Certain compounds may exist in multiple crystalline, co-crystalline, or amorphous forms. Compounds include pharmaceutically acceptable salts thereof, or pharmaceutically acceptable solvates of the free acid form of any of the foregoing, as well as crystalline forms of any of the foregoing.

"Pharmaceutically acceptable salt" refers to a salt of a compound, which possesses the desired pharmacological activity of the parent compound. Such salts include acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, and the like. In certain embodiments, a pharmaceutically acceptable salt is the hydrochloride salt. In certain embodiments, a pharmaceutically acceptable salt is the sodium salt.

"Salt" refers to a salt of a compound, including, but not limited to, pharmaceutically acceptable salts.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound provided by the present disclosure may be administered to a patient and which does not destroy the pharmacological activity thereof and which is non-toxic when administered in doses sufficient to provide a therapeutically effective amount of the compound.

"Pharmaceutical composition" refers to a compound of Formula (I) or Formula (II) and at least one pharmaceutically acceptable vehicle, with which the compound of Formula (I) or Formula (II) is administered to a patient.

"Solvate" refers to a molecular complex of a compound with one or more solvent molecules in a stoichiometric or non-stoichiometric amount. Such solvent molecules are those commonly used in the pharmaceutical art, which are known to be innocuous to a patient, e.g., water, ethanol, and the like. A molecular complex of a compound or moiety of a compound and a solvent can be stabilized by non-covalent intramolecular forces such as, for example, electrostatic forces, van der Waals forces, or hydrogen bonds. The term "hydrate" refers to a solvate in which the one or more solvent molecules is water.

"Conjugate acid of an organic base" refers to the protonated form of a primary, secondary or tertiary amine or heteroaromatic nitrogen base. Representative examples include, but are not limited to, triethylammonium, morpholinium and pyridinium.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane and the like. In some embodiments, the cycloalkyl group is ($C_3$-$C_{10}$) cycloalkyl. In other embodiments, the cycloalkyl group is ($C_3$-$C_7$) cycloalkyl.

"Cycloheteroalkyl" by itself or as part of another substituent refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidine, quinuclidine, and the like.

"Dialkylamino" by itself or as part of another substituent refers to the radical —$NR^{43}R^{44}$ where $R^{43}$ and $R^{44}$ are independently alkyl, cycloalkyl, cycloheteroalkyl, arylalkyl, heteroalkyl or heteroarylalkyl, or optionally $R^{43}$ and $R^{44}$ together with the nitrogen to which they are attached form a cycloheteroalkyl ring.

"Heteroalkyl, Heteroalkanyl, Heteroalkenyl and Heteroalkynyl" by themselves or as part of another substituent refer to alkyl, alkanyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to, —O—, —S—, —O—O—, —S—S—, —O—S—, —$NR^{45}R^{46}$, —=N—N—, —N=N—, —N=N—$NR^{47}R^{43}$, —$PR^{49}$—, —$P(O)_2$—, —$POR^{50}$—, —O—$P(O)_2$—, —SO—, —$SO_2$—, —$SnR^{51}R^{52}$— and the like, where $R^{45}$, $R^{46}$, $R^{47}$, $R^{48}$, $R^{49}$, $R^{50}$, $R^{51}$ and $R^{52}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, □-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is from 5-20 membered heteroaryl, more preferably from 5-10 membered heteroaryl. Certain heteroaryl groups are those derived from thiophene, pyrrole, benzothiophene, benzofuran, indole, pyridine, quinoline, imidazole, oxazole and pyrazine "Heteroarylalkyl" by itself or as part of another substituent refers to an acyclic alkyl radical in which one of the hydrogen atoms bonded to a carbon atom, typically a terminal or $Sp^3$ carbon atom, is replaced with a heteroaryl group. Where specific alkyl moieties are intended, the nomenclature heteroarylalkanyl, heteroarylalkenyl and/or heterorylalkynyl is used. In some embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl. In other embodiments, the heteroarylalkyl group is a 6-20 membered heteroarylalkyl, e.g., the alkanyl, alkenyl or alkynyl moiety of the heteroarylalkyl is 1-8 membered and the heteroaryl moiety is a 5-12-membered heteroaryl.

"Sulfonamido" by itself or as part of another substituent refers to a radical —$NR^{53}S(O)_2R^{54}$, where $R^{53}$ is alkyl, substituted alkyl, cycloalkyl, cycloheteroalkyl, aryl, substituted aryl, arylalkyl, heteroalkyl, heteroaryl or heteroarylalkyl and $R^{54}$ is hydrogen, alkyl, cycloalkyl, cycloheteroalkyl, aryl, arylalkyl, heteroalkyl, heteroaryl or heteroarylalkyl as defined herein. Representative examples include, but are not limited to methanesulfonamido, benzenesulfonamido and p-toluenesulfonamido.

"Aromatic Ring System" by itself or as part of another substituent refers to an unsaturated cyclic or polycyclic ring system radical having a conjugated π electron system. Specifically included within the definition of "aromatic ring system" are fused ring systems in which one or more of the rings are aromatic and one or more of the rings are saturated or unsaturated, such as, for example, fluorene, indane, indene, phenalene, etc. Typical aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Heteroaromatic Ring System" by itself or as part of another substituent refers to a aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Halo" means fluoro, chloro, bromo, or iodo radical.

"Heteroalkyloxy" means an —O-heteroalkyl where heteroalkyl is as defined herein.

"Heteroaryloxycarbonyl" refers to a radical —C(O)—OR where R is heteroaryl as defined herein.

Substituted" refers to a group in which one or more hydrogen atoms are each independently replaced with the same or different substituent(s). Typical substituents include, but are not limited to, —X, —$R^{29}$, —O⁻, =O, —$OR^{29}$, —$SR^{29}$, —S⁻, =S, —$NR^{29}R^{30}$, =$NR^{29}$, —$CX_3$, —$CF_3$, —CN, —OCN, —SCN, —NO, —$NO_2$, =$N_2$, —$N_3$, —$S(O)_2O^-$, —$S(O)_2OH$, —$S(O)_2R^{29}$, —$OS(O_2)O^-$, —$OS(O)_2R^{29}$, —$P(O)(O^-)_2$, —$P(O)(OR^{29})(O^-)$, —$OP(O)(OR^{29})(OR^{30})$, —$C(O)R^{29}$, —$C(S)R^{29}$, —$C(O)OR^{29}$, —$C(O)NR^{29}R^{30}$, —$C(O)O^-$, —$C(S)OR^{29}$, —$NR^{31}C(O)NR^{29}R^{30}$, —$NR^{31}C(S)NR^{29}R^{30}$, —$NR^{31}C(NR^{29})NR^{29}R^{30}$ and —$C(NR^{29})NR^{29}R^{30}$, where each X is independently a halogen; each $R^{29}$ and $R^{30}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl, —$NR^{31}R^{32}$, —$C(O)R^{31}$ or —$S(O)_2R^{31}$ or optionally $R^{29}$ and $R^{30}$ together with the atom to which they are both attached form a cycloheteroalkyl or substituted cycloheteroalkyl ring; and $R^{31}$ and $R^{32}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Sulfonic acids derivatives" as used herein are a class of organic acid radicals with the general formula $RSO_3H$ or $RSO_3$. An oxygen, suflur, or R moiety can serve as a point of attachment. Sulfonic acid salt derivatives substitute a cationic salt (e.g. Na⁺, K⁺, etc.) for the hydrogen on the sulfate group. In various embodiments, the deprotonated sulfonic acid group can be used as the point of attachment to a therapeutic or targeting group, optionally via a linker. Examples of sulfonic acid derivatives and include, but are not limited to, 2-methyl-2-propane-1-sulfonic acid-sodium salt, 2-sulfoethyl methacrylate, 3-phenyl-1-propene-2-sulfonic acid-p-toluidine salt, 3-sulfopropyl acrylate-potassium salt, 3-sulfopropyl methacrylate-potassium salt, ammonium 2-sulfatoethyl methacrylate, styrene sulfonic acid, 4-sodium styrene sulfonate.

"Anhydride derivatives" as used herein refer to a compound or radical having the chemical structure $R_1C(O)OC(O)R_2$. The carboxyl groups, optionally after removal of $R_1$ or $R_2$ groups, can be used as the point of attachment to a therapeutic or targeting group, optionally via a linker. Examples of anhydride derivatives include, but are not limited to, acrylic anhydride, methacrylic anhydride, maleic anhydride, and 4-methacryloxyethyl trimellitic anhydride "Hydroxyl derivative" as used herein refers to a compound or radical having the structure ROH. The deprotonated hydroxyl group can be used as the point of attachment to a therapeutic or targeting group, optionally via a linker. Example of hydroxyl derivatives include, but are not limited to, vinyl alcohol, 2-hydroxyethyl acrylate, 2-hydroxyethyl methacrylate, 2-allyl-2-methoxyphenol, divinyl glycol, glycerol monomethacrylate, poly(propylene glycol)monomethacrylate, N-(2-hydroxypropyl) methacrylamide, hydroxymethyldiacetoneacrylamide, poly(ethylene glycol)monomethacrylate, N-methacryloylglycylglycine, N-methacryloylglycyl-DL-phenylalanylleucylglycine, 4-methacryloxy-2-hydroxybenzophenone, 1,1,1-trimethylolpropane diallyl ether, 4-allyl-2-methoxyphenol, hydroxymethyldiacetoneacrylamide, N-methylolacrylamide, and sugar based monomers.

"Amine derivatives" are compound or radicals thereof having a functional group containing at least one nitrogen, and having the structure RNR'R". R, R' and R" in amine derivatives can each independently be any desired substituent, including but not limited to hydrogen, halides, and substituted or unsubstituted alkyl, alkoxy, aryl or acyl groups. "Amide derivatives" as used herein refer to compounds having the structure RC(O)NR'R". The R, R' and R" in amide derivatives can each independently be any desired substituent, including but not limited to hydrogen, halides, and substituted or unsubstituted alkyl, alkoxy, aryl or acyl groups. The amine or amide group can be used as the point of attachment to a therapeutic or targeting group, optionally via a linker. Examples of amines and amides include, but are not limited to, 2-(N,N-diethylamino)ethyl methacrylate, 2-(N,N-diethylamino)ethyl acrylate, N-[2-(N,N-dimethylamino)ethyl]methacrylamide, N-[3-(N,N-dimethylamino)propyl] acrylamide, diallylamine, methacryloyl-L-lysine, 2-(tert-butylamino)ethyl methacrylate, N-(3-aminopropyl) methacrylamide hydrochloride, 3-dimethylaminoneopentyl acrylate, N-(2-hydroxypropyl)methacrylamide, N-methacryloyl tyrosine amide, 2-diisopropylaminoethyl methacrylate, 3-dimethylaminoneopentyl acrylate, 2-aminoethyl methacrylate hydrochloride, hydroxymethyldiacetoneacrylamide, N-(iso-butoxymethyl)methacrylamide and N-methylolacrylamide.

"Silane derivative" as used herein refers to compounds or radicals thereof having at least one substituent having the structure RSiR'R"R'". R, R' and R" can each independently be any desired substituent, including but not limited to hydrogen, alkyl, alkoxy, aryl or acyl groups. The silane group can be used as the point of attachment to a therapeutic or targeting group, optionally via a linker. Examples of silane derivatives include, but are not limited to, 3-methacryloxypropyl trimethoxysilane, vinyltriethoxysilane, 2-(trimethylsiloxy) ethyl methacrylate, 1-(2-trimethylsiloxyethoxy)-1-trimethylsiloxy-2-methylpropene "Phosphate derivatives" as used herein refer to compounds or radicals thereof having at least one compound containing the structure $RR'R"PO_4$. R, R' and R" can each independently be any desired substituent, including but not limited to hydrogen, alkyl, alkoxy, aryl or acyl groups. The phosphate group can be used as the point of attachment to a therapeutic or targeting group, optionally via a linker. Examples of phosphate derivatives include, but are not limited to, monoacryloxyethyl phosphate and bis(2-methacryloxyethyl) phosphate.

"Nitro derivatives" as used herein refer to compounds or radicals thereof having an $NO_2$ group. The nitro group can be used as the point of attachment to a therapeutic or targeting group, optionally via a linker. Examples include, but are not limited to, o-nitrobenzyl methacrylate, methacryloylglycyl-DL-phenylalanyl-L-leucyl-glycine 4-nitrophenyl ester, methacryloylglycyl-L-phenylalanyl-L-leucyl-glycine 4-nitrophenyl ester, N-methacryloylglycylglycine 4-nitrophenyl ester, 4-nitrostyrene "Succinimide derivative" as used herein refers to compounds or radicals thereof having the group

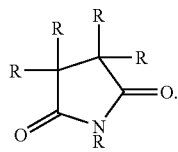

The succinyl R groups can be substituted by any substituent, for example and substituted or unsubstituted alkyl, alcoxy, aryl groups. Typically, the succinimide group is attached to a compound via a covalent bond at the nitrogen. The succinimide group can be used as the point of attachment to a therapeutic or targeting group, optionally via a linker. A succinimide derivative can be a sulfo-containing succinimide derivative. N-acryloxysuccinimide is an exemplary succinimide derivative.

"Halide derivatives" as used herein refer to compounds or radicals thereof having a halide substituent. The halide group can be used as the point of attachment to a therapeutic or targeting group, optionally via a linker. Examples include, but are not limited to, vinyl chloride, 3-chlorostyrene, 2,4,6-tribromophenyl acrylate, 4-chlorophenyl acrylate, 2-bromoethyl acrylate. Non-limiting examples include, but are not limited to, divinylbenzene, ethylene glycol diacrylate, N,N-diallylacrylamide, and allyl methacrylate.

"Morpholine derivatives" as used herein refer to compounds or radicals thereof having the structure:

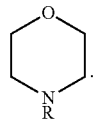

Typically, the amine group serves as the point of attachment to other compounds. The morpholine group can be used as the point of attachment to a therapeutic or targeting group, optionally via a linker. Examples of morpholine derivatives include, but are not limited to, N-acryloylmorpholine, 2-N-morpholinoethyl acrylate and 2-N-morpholinoethyl methacrylate.

"Cyano derivatives" as used herein refer to compounds or radicals thereof having the structure RCN. R can each independently be any desired substituent. The cyano group can be used as the point of attachment to a therapeutic or targeting group, optionally via a linker. Examples of cyano derivatives include, but are not limited to, 2-cyanoethyl acrylate.

"Epoxide derivatives" as used herein refer to compounds or radicals thereof having the following chemical structure:

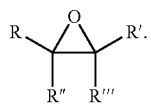

R, R', R", and R''' can each independently be any desired substituent. The epoxide group can be used as the point of attachment to a therapeutic or targeting group, optionally via a linker. Examples of epoxide derivatives include, but are not limited to, glycidyl methacrylate.

"Ester derivatives" as used herein refer to a compound or a radical thereof having the generic chemical structure RC(O)OR'. R and R' can each independently be any desired substituent. The ester group can be used as the point of attachment to a therapeutic or targeting group, optionally via a linker. Examples include, but are not limited to, methyl acrylate, methyl methacrylate, tert-butyl acrylate, tert-butyl methacrylate, vinyl acetate, benzyl acrylate and benzyl methacrylate.

"Ether derivatives" as used herein refer to a compound or a radical thereof having the generic chemical structure R—O—R'. The ether group can be used as the point of attachment to a therapeutic or targeting group, optionally via a linker. Examples include, but are not limited to, methyl vinyl ether, butyl vinyl ether, 2-chloroethyl vinyl ether, cyclohexyl vinyl ether.

"Carbazole derivatives" as used to herein refer to a compound or radical thereof having the structure

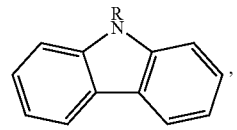

and any substitutions at any site thereof. The carbazole group can be used as the point of attachment to a therapeutic or targeting group, optionally via a linker. Examples of carbazole derivatives include but are not limited to, N-vinylcarbazole.

"Azide derivatives" as used herein refer to a compound or a radical thereof having the structure N=N=N. The azide group can be used as the point of attachment to a therapeutic or targeting group, optionally via a linker. Examples of azide derivatives include, but are not limited to, 2-hydroxy-3-azidopropyl methacrylate, 2-hydroxy-3-azidopropyl acrylate, 3-azidopropyl methacrylate.

The term "maleimide derivative" as referred to herein refers to a compound or a radical thereof having the structure:

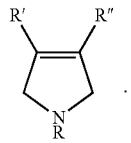

R, R' and R" can each independently be any desired substituent.

The term "thiolate" refers to a compound or radical thereof having a —SR structure, where R can be any desired substituent.

The term "thioether" refers to a compound or radical thereof having the structure R—S—CO—R', where R and R' can each independently be any desired substituent.

The term "thioester" refers to a compound or radical thereof having the structure R—S—CO—R', where R and R' can each independently be any desired substituent.

The term "carboxylate" refers to a compound or radical thereof having the structure RCOO—, where R can be any desired substitutent.

The term "phosphonate" refers to a compound or radical thereof having the structure R—PO(OH)$_2$ or R—PO(OR')$_2$. where R and R' can each independently be any desired substituent.

The term "phosphinate" refers to a compound or radical thereof having the structure OP(OR)R'R" where R, R' and R" can each independently be any desired substituent.

The term "sulphonate" refers to a compound or radical thereof having the structure RSO$_2$O$^-$ where R can be any desired substituent.

The term "sulphate" refers to a compound or radical thereof having the structure RSO$_4$. where R can be any desired substituent.

A "reducing agent" is an element or a compound that reduces another species. Exemplary reducing agents include, but are not limited to, ferrous ion, lithium aluminium hydride (LiAlH$_4$), potassium ferricyanide (K$_3$Fe(CN)$_6$), sodium borohydride (NaBH$_4$), sulfites, hydrazine, diisobutylaluminum hydride (DIBAH), primary amines, and oxalic acid (C$_2$H$_2$O$_4$).

"Treating" or "treatment" of any disease or disorder refers, in some embodiments, to ameliorating the disease or disorder (i.e., arresting or reducing the development of the disease or at least one of the clinical symptoms thereof). In other embodiments "treating" or "treatment" refers to ameliorating at least one physical parameter, which may not be discernible by the patient. In yet other embodiments, "treating" or "treatment" refers to inhibiting the disease or disorder, either physically, (e.g., stabilization of a discernible symptom), physiologically, (e.g., stabilization of a physical parameter), or both. In still other embodiments, "treating" or "treatment" refers to delaying the onset of the disease or disorder.

The term "antibody" refers to a monomeric or multimeric protein comprising one or more polypeptide chains that binds specifically to an antigen. An antibody can be a full length antibody or an antibody fragment.

By "full length antibody," herein is meant the structure that constitutes the natural biological form of an antibody, including variable and constant regions. For example, in most mammals, including humans and mice, the full length antibody of the IgG class is a tetramer and consists of two identical pairs of two immunoglobulin chains, each pair having one light and one heavy chain, each light chain comprising immunoglobulin domains $V_L$ and $C_L$, and each heavy chain comprising immunoglobulin domains $V_H$, CH1 (Cγ1), CH2 (Cγ2), and CH3 (Cγ3). In some mammals, for example in camels and llamas, IgG antibodies may consist of only two heavy chains, each heavy chain comprising a variable domain attached to the Fc region.

"Antibody fragments" are portions of full length antibodies that bind antigens. Specific antibody fragments include, but are not limited to, (i) the Fab fragment consisting of VL, VH, CL and CH1 domains, (ii) the Fd fragment consisting of the VH and CH1 domains, (iii) the fv fragment consisting of the VL and VH domains of a single antibody; (iv) the dAb fragment (Ward et al., 1989, Nature 341:544-546) which consists of a single variable, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988, Science 242:423-426, Huston et al., 1988, Proc. Natl. Acad. Sci. U.S.A. 85:5879-5883), (viii) bispecific single chain Fv dimers (PCT/US92/09965) and (ix) "diabodies" or "triabodies", multivalent or multispecific fragments constructed by gene fusion (Tomlinson et. al., 2000, Methods Enzymol. 326:461-479; WO94/13804; Holliger et al., 1993, Proc. Natl. Acad. Sci. U.S.A. 90:6444-6448). In certain embodiments, antibodies are produced by recombinant DNA techniques. Other examples of antibody formats and architectures are described in Holliger & Hudson, 2006, Nature Biotechnology 23(9):1126-1136, and Carter 2006, Nature Reviews Immunology 6:343-357 and references cited therein, all expressly incorporated by reference. In additional embodiments, antibodies are produced by enzymatic or chemical cleavage of naturally occurring antibodies.

Nanoparticles

The present disclosure is directed to modified lanthanide nanoparticles, particularly gadolinium nanoparticles. The term "nanoparticle" as referred to herein means a particle including lanthanide, such as gadolinium (III), nanoparticles having at least one special dimension measurable less than a micron in length. Nanoparticles include conventionally known nanoparticles such as nanorods, nanospheres and nanoplatelets. In various embodiments, for example, nanospheres can be a rod, sphere, or any other three dimensional shape. Nanoparticles are generally described, for example, in Burda et al., Chem. Rev. 2005, 105, 10251102.

The nanoparticle conjugates described herein are generally described as gadolinium nanoparticles and gadolinium nanoparticle conjugates. However, the descriptions provided herein may be applied equally and fully to other lanthanide nanoparticles. In this context, lanthanides include Gadolinium, Lanthanum, Erbium, Ytterbium, Neodymium, Europium, Terbium, Cerium, Thulium, Praseodymium, Promethium, Samarium, Dysprosium, Holmium, and Lutetium.

Gadolinium Nanoparticles

Gadolinium nanoparticles containing gadolinium (III) function as MRI contrast agents. Gadolinium enhances the image contrast by increasing water proton relaxation rates. When conjugated to targeting agents, gadolinium nanoparticles are effective site-specific MRI contrast agents owing to their large metal payload.

"Gadolinium nanoparticle" as used herein refers to a nanoparticle containing gadolinium (III) Gd$^{3+}$. Gadolinium nanoparticles include, but are not limited to, gadolinium (III) metal-organic frameworks such as those containing carboxylic acids, ligands, and polymers. Representative examples of gadolinium (III) nanoparticles include Gd(1,4-benzenedicarboxylate)1.5(H$_2$O)$_2$ (also known as Gd(1,4-BDC)1.5 (H$_2$O)$_2$), Gd$_2$O$_3$, gadolinium nitrate and emulsions thereof, and gadolinium fluoride.

Gadolinium nanoparticles can be synthesized by any method known in the art. In a certain embodiment, the gadolinium particles are synthesized as described in, e.g., Rieter, W. J.; et al. J. Am. Chem. Soc. 2006 128, 9024-9025.

The quantity of gadolinium (III) in gadolinium nanoparticles can be controlled as described in the art by controlling reaction conditions. For example, in the case of Gd(1,4-BDC) 1.5(H$_2$O)$_2$ nanoparticle synthesis as described in, e.g., Rieter, W. J. et al., J. Am. Chem. Soc. 2006 128, 9024-9025, the morphologies and sizes of the nanorods can be controlled and influenced by the water/surfactant molar ratio, microemulsion precursors, reactant concentration and the reactant ratio.

In alternative embodiments, gadolinium nanoparticles can be synthesized to have a core-shell morphology with a functionalized polymer on the surface. For example, gadolinium nanoparticles can be synthesized as described in Reynolds *J. Am. Chem. Soc.* 2000, 122, 8940-8945 Alternatively, gadolinium nanoparticles having a paramagnetic Gd$_2$O$_3$ core can be produced by encapsulating Gd$_2$O$_3$ cores within a polysiloxane shell which carries organic fluorophores and carboxylated PEG covalently tethered to the inorganic network as described in Bridot et al., J. Am. Chem. Soc.; (Article); 2007; 129(16); 5076-5084. In other embodiments, the gadolinium nanoparticles can be synthesized as inorganic/organic hybrid molecules, as described in Hifumi et al. *J. Am. Chem. Soc.,* 128 (47), 15090-15091, 2006.

The quantity of gadolinium in a gadolinium nanoparticle can be modified to adjust contrast in MRI techniques. For example, the quantity of gadolinium in a gadolinium nanoparticle can be optimized for resonance imaging techniques for imaging techniques such as magnetic resonance imaging (MRI). The quantity of gadolinium nanoparticles can be adjusted for, for example, in Ahrens et al., PNAS 95(15) 8443-8448 (1998). Various parameters of gadolinium nanoparticles can be modified. Parameters include the concentration of gadolinium (III), size, aspect ratio, and surface-to-volume concentration of gadolinium (III) in the nanoparticle as described in e.g. Rieter, W. J. et al., J. Am. Chem. Soc. 2006 128, 9024-9025.

Forming Initiators on the Nanoparticle Surface

Prior to growing polymers on the surface of Gd nanoparticles, the nanoparticle can be treated to form imperfections (or initiators) on the nanoparticle surface that facilitate polymer formation or polymer precursor binding.

Polymerization

Polymerization can be performed by any method known in the art. Polymerization methods that can be used are described in Principles of Polymerization, 4th edition (2004) by George Odian, Published by Wiley-Interscience, which is incorporated herein by reference in its entirety. Various methods of polymerization include RAFT, Atom Transfer Radical Polymerization (ATRP), Stable Free Radical Polymerization (SFRP), and conventional free radical polymerization.

Reversible addition-fragmentation chain transfer (RAFT) polymerization operates on the principle of degenerative chain transfer. Without being limited to a particular mechanism, Scheme 1 shows a proposed mechanism for RAFT polymerization. In Scheme 1, RAFT polymerization involves a single- or multi-functional chain transfer agent (CTA), such as the compound of formula (I), including dithioesters, trithiocarbonates, xanthates, and dithiocarbamates. The initiator produces a free radical, which subsequently reacts with a polymerizable monomer. The monomer radical reacts with other monomers and propagates to form a chain, Pn*, which can react with the CTA. The CTA can fragment, either forming R*, which will react with another monomer that will form a new chain $P_m^*$ or $P_n^*$, which will continue to propagate. In theory, propagation to the $P_m^*$ and $P_n^*$ will continue until no monomer is left or a termination step occurs. After the first polymerization has finished, in particular circumstances, a second monomer can be added to the system to form a block copolymer.

Scheme 1

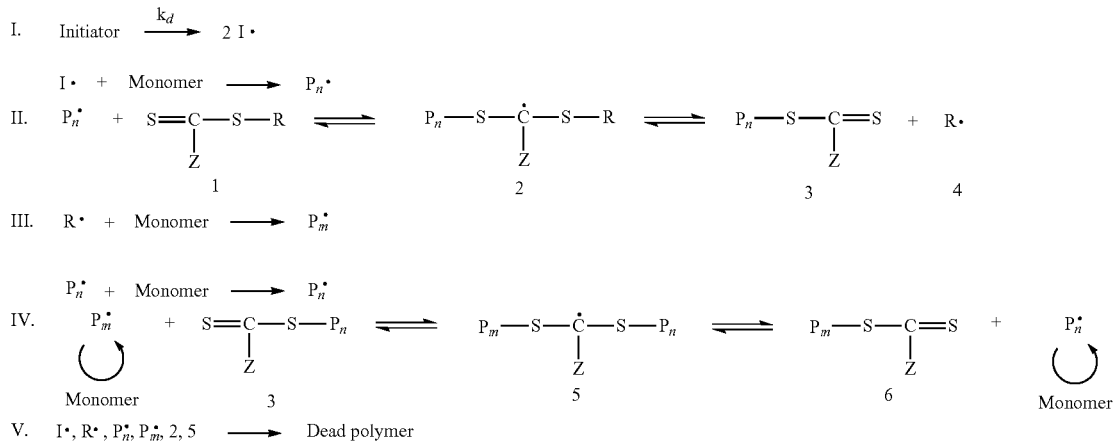

RAFT polymerization involves a similar mechanism as traditional free radical polymerization systems, with the difference of a purposely added CTA. Addition of a growing chain to a macro-CTA yields an intermediate radical, which can fragment to either the initial reactants or a new active chain. With a high chain transfer constant and the addition of a high concentration of CTA relative to conventional initiator, synthesis of polymer with a high degree of chain-end functionality and with well defined molecular weight properties is obtained.

In particular embodiments, RAFT polymerization is used to produce a variety of well-defined, novel polymers that either are polymerized from the surface of the nanoparticles, or are polymerized and then attached to the surface of the nanoparticle. RAFT polymerization shows great promise in the synthesis of multifunctional polymers due to the versatility of monomer selection and polymerization conditions, along with the ability to produce well-defined, narrow polydispersity polymers with both simple and complex architectures. For example, RAFT can be successfully used to produce well-defined activated biocopolymer constructs with N-acryloxysuccinimide (NAOS) pendant functionalities. The succinimide side groups have allowed covalent conjugation of bioactive agents such as fluorescent tags, nucleotides, peptides, and antibodies.[5-6] Incorporation of NAOS into copolymers provides a route of manipulating loading efficiency and stability of bioactive agents. Additional tailoring of the copolymer conjugate system with tumor targeting or therapeutic agents allows specific localization and treatment to be achieved increasing in vivo performance.

Polymers synthesized by RAFT include chain transfer agents (CTAs). As used herein, a RAFT chain transfer agent is defined as having the chemical structure of Formula (IV):

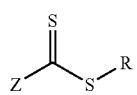

(IV)

CTAs agents possessing the thiocarbonylthio moiety, impart reactivity to free-radical polymerization due to the facile nature of radical addition to C=S bonds which contributes to faster chain equilibration in the chain transfer step. The transfer constants of RAFT CTAs depend on the Z and R substituents. In certain embodiments, the Z group is a free radical stabilizing species to ensure rapid addition across the C=S bond.

In certain embodiments, the R group is chosen so that it possesses an equal or greater ability to leave as compared to the addition species. It is also of importance that the R group be able to reinitiate the polymerization after fragmentation. In certain embodiments, R can fragment from the intermediate quickly and is able to re-initiate polymerization effectively.

Exemplary CTAs include, but are not limited to, cumyl dithiobenzoate (CDTB) and S-1-Dodecyl-S'-(α,α'-dimethyl-α"-acetic acid)trithiocarbonate (DATC).

Grafting Polymers and Polymer Precursors to Nanoparticles

In certain aspects, polymers can be grafted to the gadolinium nanoparticles after polymerization. Optimal choice of CTA structures of formula (I) allows for control of the polymerization. The Z group activates the thio-carbonyl (C=S) group for radical addition and allows for the radical intermediate to be stabilized in the transition state.

Schemes 2 and 3 show grafting trithiocarbonate and dithioester RAFT agents to the surface of a gadolinium nanoparticle. Scheme 2 shows first RAFT polymerization of the alkene in the presence of the trithiocarbonate, and Scheme 3 shows a first step of RAFT polymerization of the alkene in the presence of the dithioester.

The RAFT polymer is grafted to the surface of the nanoparticle. Without being limited to any particular mechanism, the nanoparticle is covalently grafted to the nanoparticle surface. The reduced polymer is covalently grafted to the nanoparticle.

Scheme 2

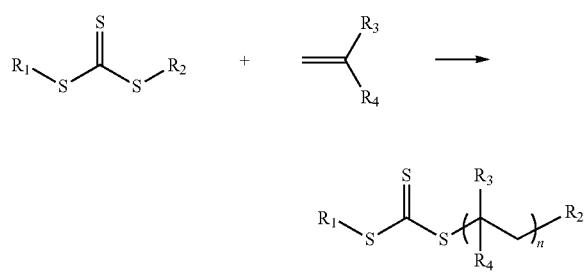

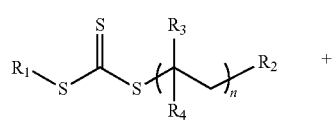

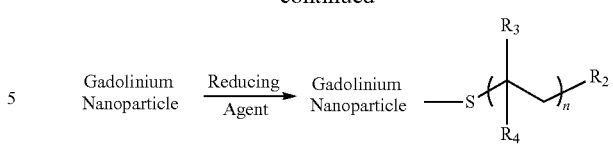

Scheme 3

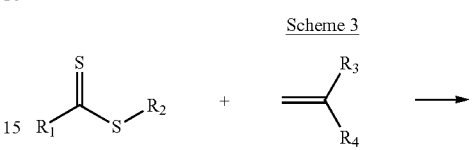

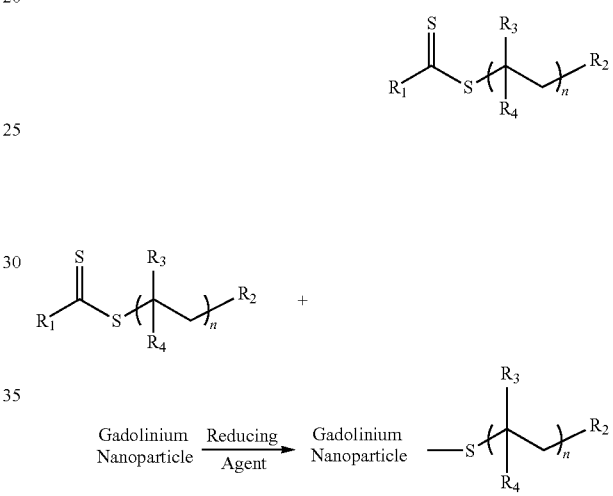

In Schemes 2 and 3, $R_1$, $R_2$, $R_3$, and $R_4$ are each independently selected from hydrogen, alkyl, substituted alkyl, alkoxy, substituted alkoxy, acyl, substituted acyl, acylamino, substituted acylamino, alkylamino, substituted alkylamino, alkylsulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, aryloxycarbonyl, substituted aryloxycarbonyl, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy and substituted heteroaryloxy.

A specific example of RAFT polymers attached to the surface of the gadolinium particle after polymerization is depicted in Scheme 4 below.

The modified polymer can be added to the gadolinium nanoparticle after reduction of the trithiocarbonate group to a thiol to produce a gadolinium nanoparticle conjugate. Scheme 4 depicts a method of attaching a modified polymer to a gadolinium nanoparticle to produce a gadolinium nanoparticle conjugate.

Scheme 4

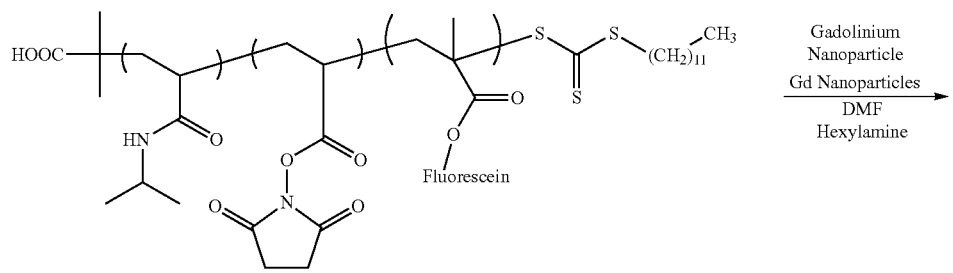

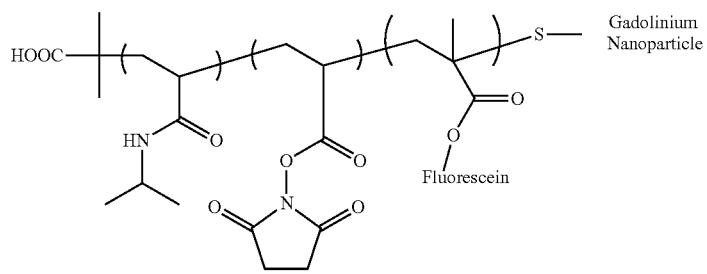

Grafting From Nanoparticles

In the two examples of generalized RAFT polymerization described above in Schemes 2 and 3, as well as the specific example in Scheme 4, polymerization occurs prior to grafting to the gadolinium nanoparticle surfaces (i.e. "grafting to" the nanoparticle surface).

Alternatively, the RAFT polymerization may be accomplished after grafting a polymer precursor, initiator, or CTA to the nanoparticle surface. Scheme 5 depicts attachment of a CTA to a surface-bound RAFT polymerization. In brief, a polymer precursor is grafted to the surface of the nanoparticle. A CTA is attached to the terminus of the polymer precursor in Step 1. RAFT polymerization is then accomplished in Step 2 directly from the surface of the gadolinium nanoparticle, as described, for example, in Rowe-Konopacki, M. D. and Boyes, S. G. *Synthesis of Surface Initiated Diblock Copolymer Brushes from Flat Silicon Substrates Utilizing the RAFT Polymerization Technique. Macromolecules,* 40 (4) 879-888, 2007, and Rowe, M. D.; Hammer, B. A. G.; Boyes, S. G. *Synthesis of Surface-Initiated Stimuli-Responsive Diblock Copolymer Brushes Utilizing a Combination of ATRP and RAFT Polymerization Techniques. Macromolecules,* 41 (12), 4147-4157, 2008.

Scheme 5

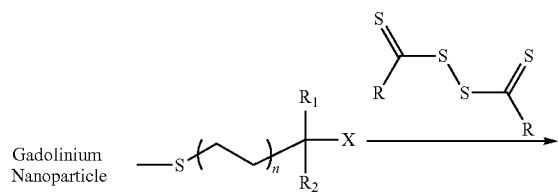

-continued

In Scheme 5, n is an integer, and X, R, $R_1$, $R_2$, $R_3$, and $R_4$ are each independently selected from hydrogen, alkyl, substituted alkyl, alkoxy, substituted alkoxy, acyl, substituted acyl, acylamino, substituted acylamino, alkylamino, substituted alkylamino, alkylsulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy and substituted heteroaryloxy. In certain embodiments, X is a halide such as fluorine, bromine, chlorine and iodine. A specific example of the reaction of Scheme 5 is depicted in Scheme 6.

Scheme 6

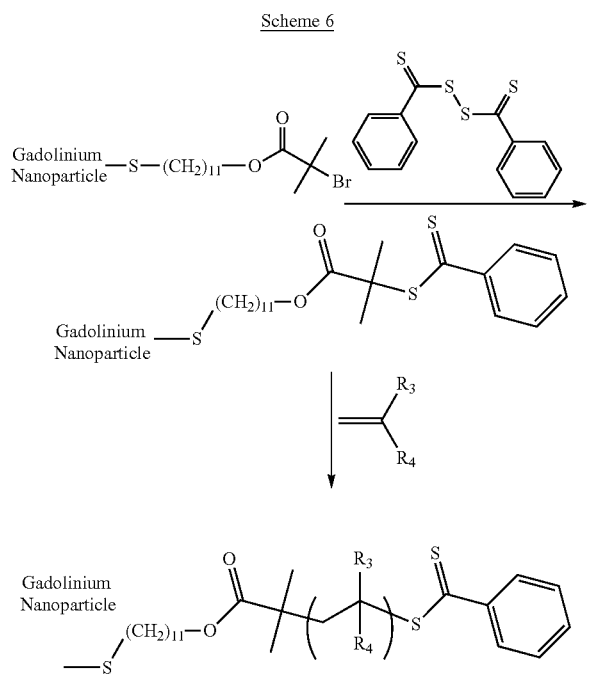

$R_3$ and $R_4$ are each independently selected from hydrogen, alkyl, substituted alkyl, alkoxy, substituted alkoxy, acyl, substituted acyl, acylamino, substituted acylamino, alkylamino, substituted alkylamino, alkylsulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, aryloxycarbonyl, substituted aryloxycarbonyl, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy and substituted heteroaryloxy.

Figure 2:
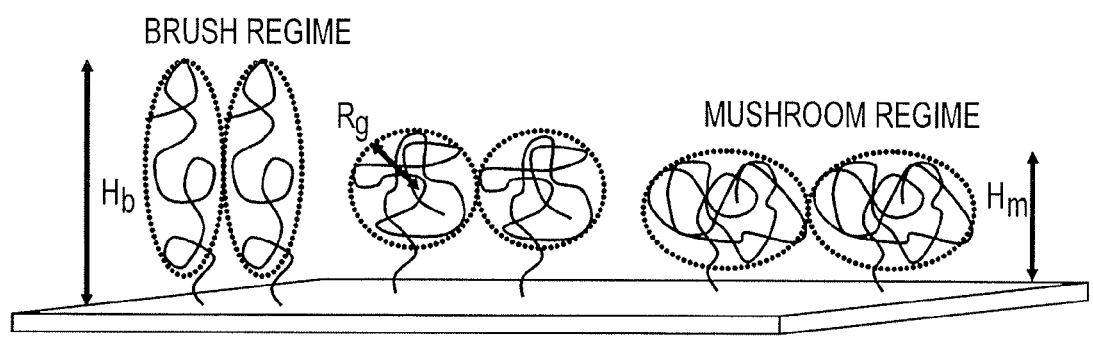
FIG. 2 depicts the mushroom to brush spatial transition of polymers at a surface.

Grafting from the surface of the nanoparticle as depicted above allows formation of a "brush" configuration of polymers. With reference to FIG. 2, polymers attached to a gadolinium surface can be spaced differently on a surface. Without wishing to be held to a specific theory or mechanism of action, the accessibility of the therapeutic agents and targeting agents to the surrounding environment can be at least partially controlled by how closely together the polymers are spaced on the surface of the nanoparticle. When the distance between the polymers is greater than the length of the polymer, the polymers adopt a "mushroom" configuration in which the entirety of the polymer can be accessible to surrounding environment, including the binding site of a targeting agent or therapeutic agent attached to the polymer. Conversely, when the distance between the polymer chains is shorter than the attached polymer, the polymers have a brush conformation, in which the terminal portions of the polymer are accessible to the surrounding environment. If the therapeutic and/or targeting agents are attached to the terminus of the polymers arranged in a "brush" conformation, then the therapeutic and/or targeting agents can be accessible to the surrounding environment.

Desired polymer configuration on the surface can be achieved by growing the polymers from the surface of the nanoparticle. In certain aspects, the polymerization is initiated directly from substrate via immobilized initiators. The brush polymer conformation can be achieved by forming the polymer from the nanoparticle surface, or alternatively by utilizing separately or combining atom transfer radical polymerization (ATRP) and RAFT polymerization. Growing the polymers from the surface allows immobilized polymerization initiators to be tailored for a wide range of polymerization techniques and substrates.

In particular, synthesizing polymer brushes requires control of the polymer molecular weight (i.e. brush thickness), narrow polydispersities and control of the composition. In the two examples of generalized RAFT polymerization described above in Schemes 5 and 6, polymerization occurs prior to grafting to the gadolinium nanoparticle surfaces (i.e. "grafting to" the nanoparticle surface).

Functional Groups

Functional groups are groups that can be covalently linked to the polymer and/or covalently linked to the therapeutic or targeting agents, and/or bonded to the nanoparticles. The functional groups include any group that can be reacted with another compound to form a covalent linkage between the compound and the polymer extending from the nanoparticle. Exemplary functional groups can include carboxylic acids and carboxylic acid salt derivatives, acid halides, sulfonic acids and sulfonic acid salts, anhydride derivatives, hydroxyl derivatives, amine and amide derivatives, silane derivations, phosphate derivatives, nitro derivatives, succinimide and sulfo-containing succinimide derivatives, halide derivatives, alkene derivatives, morpholine derivatives, cyano derivatives, epoxide derivatives, ester derivatives, carbazole derivatives, azide derivatives, alkyne derivatives, acid containing sugar derivatives, glycerol analogue derivatives, maleimide derivatives, protected acids and alcohols, and acid halide derivatives. The functional groups can be substituted or unsubstituted, as described herein.

Functional groups can be attached to the polymer during polymerization as depicted herein.

Alternatively, functional groups can be attached to the polymer backbone via a linker. The term "linker" as used herein refers to any chemical structure that can be placed between the polymer and functional group. For example, linkers include a group including alkyl, substituted alkyl, alkoxy, substituted alkoxy, acyl, substituted acyl, acylamino, substituted acylamino, alkylamino, substituted alkylamino, alkylsulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy and substituted heteroaryloxyalkyl groups. In various non-limited exemplary embodiments, the groups can be from C1 to C10, C20, or C30.

In various embodiments, the linker can include a conjugated bond, preferably selected from acetylene (—C≡C—, also called alkyne or ethyne), alkene (—CH═CH—, also called ethylene), substituted alkene (—CR═CR—, —CH═CR— and —CR═CH—), amide (—NH—CO— and —NR—CO— or —CO—NH— and —CO—NR—), azo (—N═N—), esters and thioesters (—CO—O—, —O—CO—, —CS—O— and —O—CS—) and other conjugated bonds such as (—CH═N—, —CR═N—, —N=CH— and —N=CR—), (—SiH=SiH—, —SiR=SiH—, —SiR=SiH—, and —SiR=SiR—), (—SiH=CH—, —SiR=CH—, —SiH=CR—, —SiR=CR—, —CH=SiH—, —CR=SiH—, —CH=SiR—, and —CR=SiR—). Particularly certain bonds are acetylene, alkene, amide, and substituted derivatives of these three, and azo. The linker could also be carbonyl, or a heteroatom moiety, wherein the heteroatom is selected from oxygen, sulfur, nitrogen, silicon or phosphorus. Thus, suitable heteroatom moieties include, but are not limited to, —NH and —NR, wherein R is as defined herein; substituted sulfur; sulfonyl (—SO$_2$—) sulfoxide (—SO—); phosphine oxide (—PO— and —RPO—); and thiophosphine (—PS— and —RPS—). The linker could also be a peptidyl spacer such as Gly-Phe-Leu-Gly.

Therapeutic Agents and Targeting Agents

Figure 13:
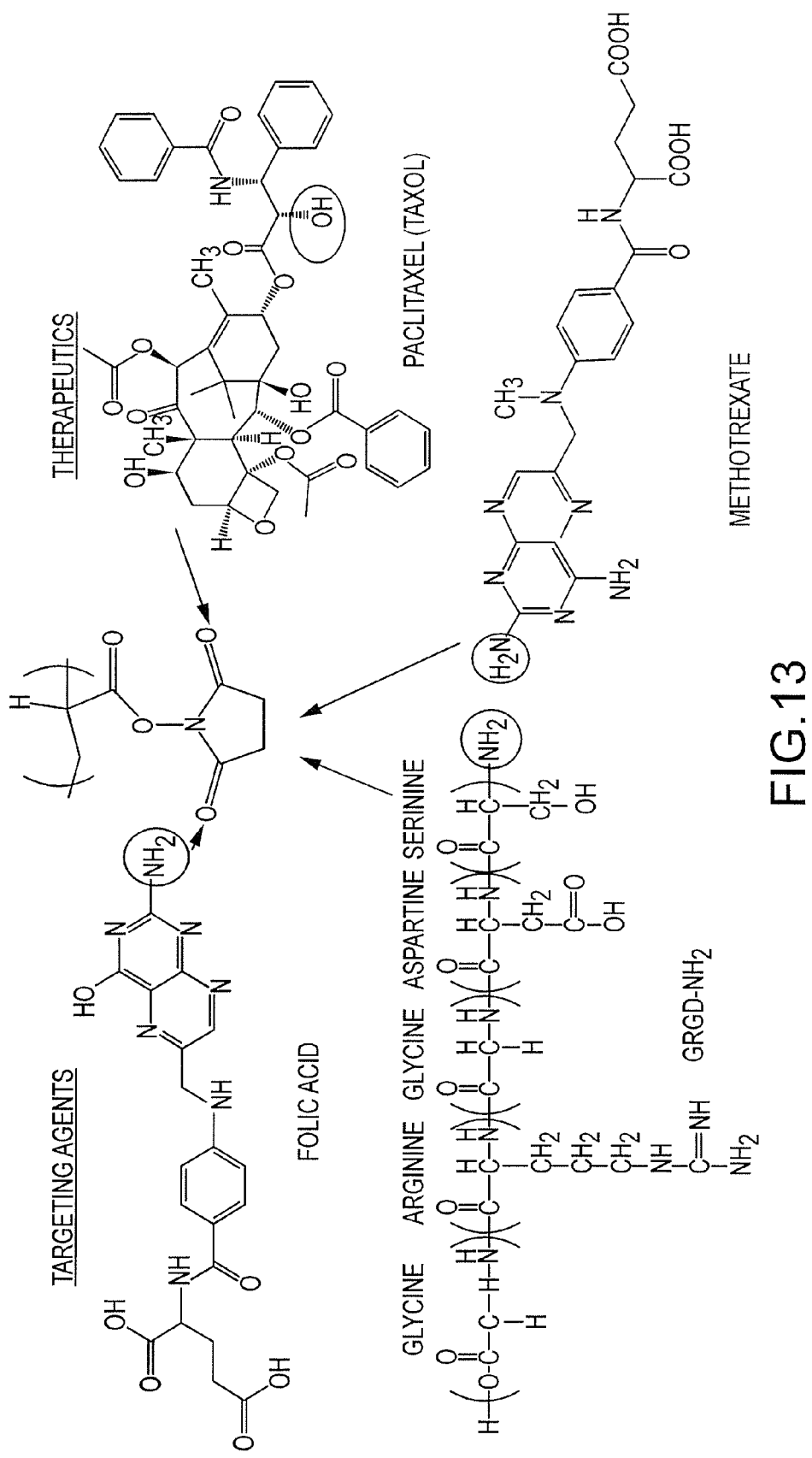
FIG. 13 depicts exemplary targeting molecules (folic acid or an RGD sequence) and exemplary therapeutic agents (the cancer therapeutics paclitaxel or methotrexate) binding to a functionalized polymer grafted to a nanoparticle.
Figure 14A:
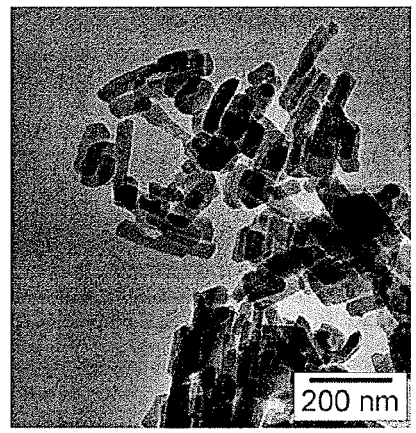
FIGS. 14(a-i) depict Transmission Electron Microscopy (TEM) images of (a) Gd NPs synthesized at 0.05M CTAB, 0.05M GdCl₃, 0.075M 1,4-BDC, with heptane and hexanol at room temperature, (b) Gd NPs synthesized at 0.05M CTAB, 0.05M GdCl₃, 0.075M 1,2,4-BTC, with heptane and hexanol at room temperature, (c) Gd NPs synthesized at 0.05M CTAB, 0.1M GdCl₃, 0.075M 1,4-BDC, with heptane and hexanol at room temperature, (d) Gd NPs synthesized at 0.05M CTAB, 0.25M GdCl₃, 0.075M 1,4-BDC, with heptane and hexanol at room temperature, (e) Gd NPs synthesized at 0.05M CTAB, 0.05M GdCl₃, 0.15M 1,4-BDC, with heptane and hexanol at room temperature, (f) Gd NPs synthesized at 0.05M CTAB, 0.10M GdCl₃, 0.15M 1,4-BDC, with heptane and hexanol at room temperature, (g) Gd NPs synthesized at 0.05M CTAB, 0.05M GdCl₃, 0.075M 1,4-BDC, with heptane and hexanol at 40° C., (h) Gd NPs synthesized at 0.05M DTAB, 0.05M GdCl₃, 0.075M 1,4-BDC, with heptane and hexanol at room temperature, (i) Gd NPs synthesized at 0.05M CTAB, 0.05M GdCl₃, 0.075M 1,4-BDC, with heptane and isopropanol at room temperature, and Gd NPs synthesized at 0.05M CTAB, 0.05M GdCl₃, 0.075M 1,4-BDC.
Figure 14B:
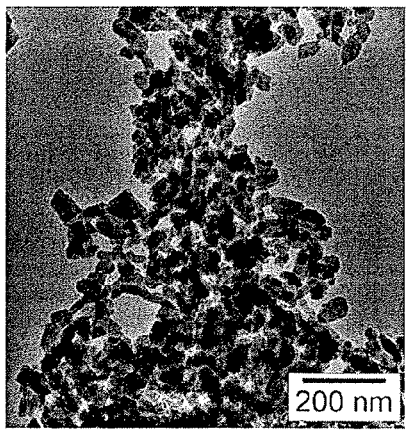
Figure 14C:
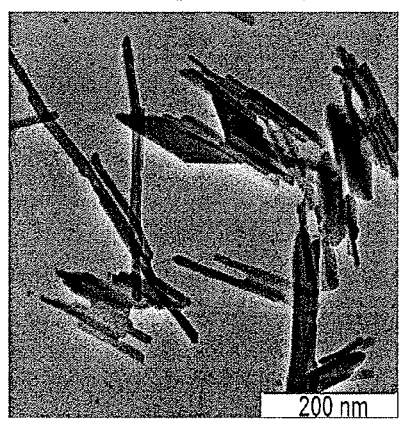
Figure 14D:
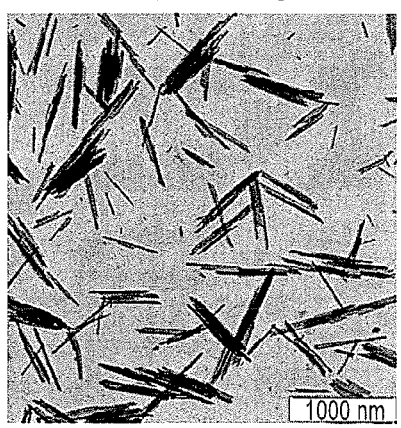
Figure 14E:
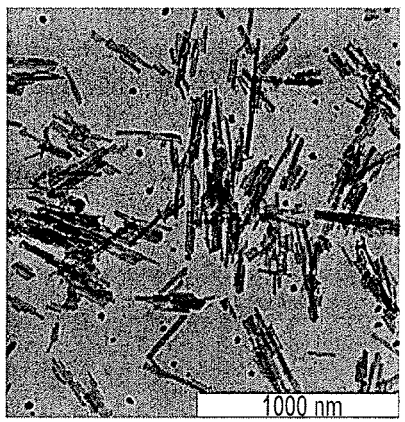
Figure 14F:
Figure 14G:
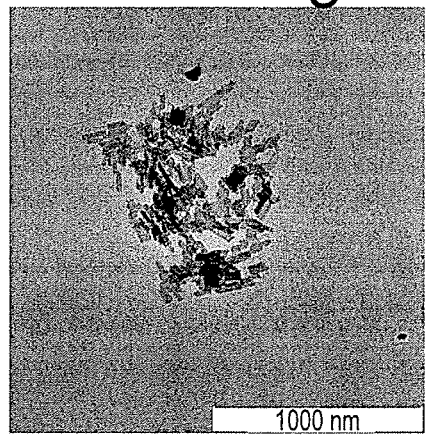
Figure 14H:
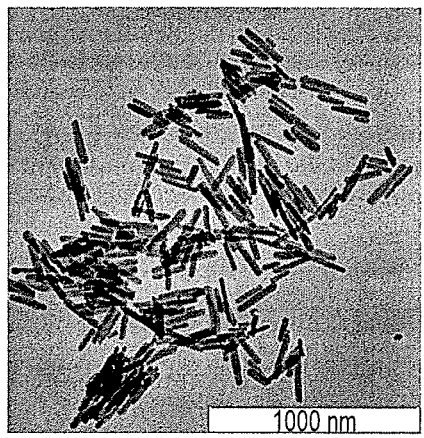
Figure 14I:
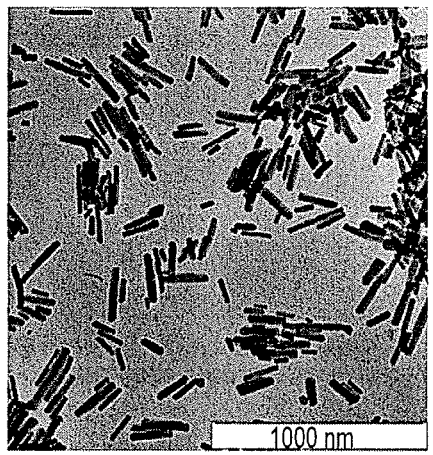

Targeting agents and therapeutic agents can be covalently attached to the polymer. FIG. 13 shows an example targeting molecules (folic acid or an RGD sequence) and an example therapeutic agents (the cancer therapeutics paclitaxel or methotrexate) binding to a functionalized polymer grafted to a nanoparticle. The functional groups attach to the polymer backbone by reaction with the succinimide functional group. Conjugation of therapeutic, targeting, and imaging agents to the copolymer provides a multifaceted system, which has potential in decreasing toxicity while increasing efficacy of the drug due to directed treatment through directed targeting with the ability to image through optical, magnetic resonance, or computer tomography.

It will be understood by those of skill in the art that various targeting agents or therapeutic agents can be selected for attachment to functional groups. Further, it will be understood that a linker can be placed between the functional groups and the targeting agents and therapeutic agents. The linker can be cleavable or non-cleavable. For example, in certain instances therapeutic agents can be cleavable. In certain instances, diagnostic agents can be non-cleavable.

Targeting agents are compounds with a specific affinity for a target compound, such as a cell surface epitope associated with a specific disease state. Targeting agents may be attached to a nanoparticle surface to allow targeting of the nanoparticle to a specific target. Non-limiting examples of targeting agents include an amino acid sequence including the RGD peptide, an NGR peptide, folate, Transferrin, GM-CSF, Galactosamine, peptide linkers including growth factor receptors (e.g. IGF-1R, MET, EGFR), antibodies and antibody fragments including anti-VEGFR, Anti-ERBB2, Anti-tenascin, Anti-CEA, Anti-MUC1, Anti-TAG72, mutagenic bacterial strains, and fatty acids.

In various embodiments, targeting agents can be chosen for the different ways in which they interact with tumors. For example, when the targeting agent folic acid is taken into the cells by the folate receptors, RGD receptors are expressed on the surface of the cells, resulting in the nanostructures localizing to the cell surface. The folate receptor is known to be over expressed in cancer cells in the case of epithelial malignancies, such as ovarian, colorectal, and breast cancer, whereas in most normal tissue it is expressed in very low levels.

Therapeutic agents include any therapeutic compounds that are capable of preventing or treating a disease in a patient. Numerous therapeutic agents are known in the art. Non-limiting examples of therapeutic agents include doxorubicin, paclitaxel, methotrexate, cisplatin, camptothecin, vinblastine, aspartic acid analogues, and short interfering ribonucleic acid (siRNA) molecules.

Therapeutic agents and targeting agents can be covalently attached to the polymer by RAFT synthesis. The therapeutic agent or targeting agent is configured to be added to the RAFT polymer during polymerization. As such the therapeutic agent and targeting agent can be linked directly to the RAFT polymer. Those of skill in the art will recognize that a linker can be added between the therapeutic agent or targeting agent and the polymer.

Alternatively, therapeutic agents and targeting agents are linked to the polymer via a functional group as described above. Those of skill in the art will recognize that a linker can be added between the therapeutic agent or targeting agent and the polymer.

Multifunctional synthesis of compounds can be accomplished by RAFT polymerization as depicted in the example of Scheme 7.

Scheme 7

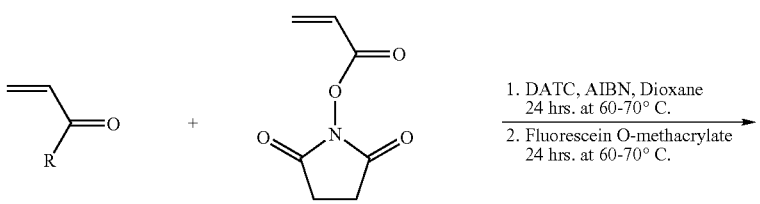

1. DATC, AIBN, Dioxane
   24 hrs. at 60-70° C.
2. Fluorescein O-methacrylate
   24 hrs. at 60-70° C.

@ 25, 33, 50% wt.

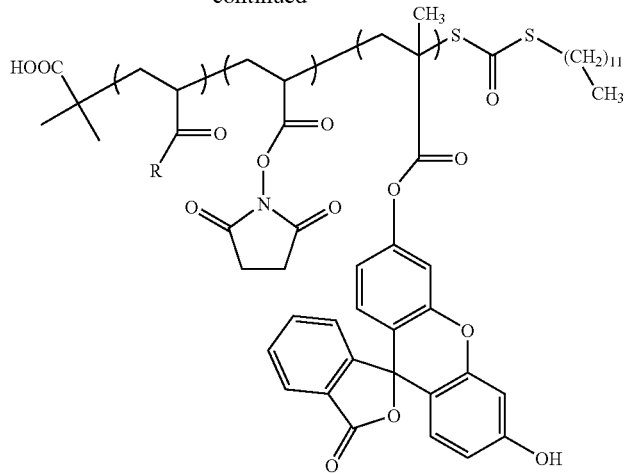

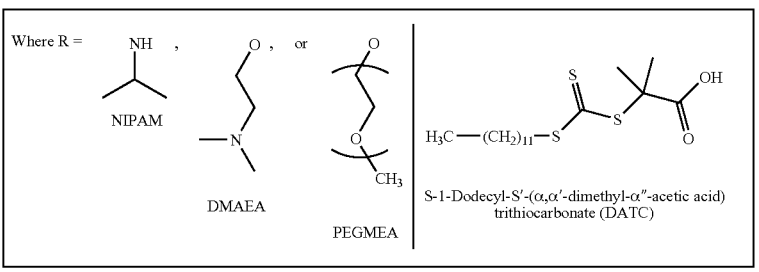

In this embodiment, a succinimide group can be used to attach a functional group to the nanoparticle. An example of biocompatible copolymers containing functional N-acryloyloxysuccinimide (NAOS) monomer units can also be synthesized via RAFT polymerization. A range of copolymer backbones can be used, including, but not limited to, N-isopropylacrylamide (NIPAM), N,N-dimethylaminoethyl acrylate (DMAEA), and poly(ethylene glycol) methyl ether acrylate (PEGMEA). The addition of NAOS into the copolymer backbones has been achieved at a range of weight percents as a means of attachment. The copolymers were synthesized utilizing the well-known trithiocarbonate DATC in dioxane at 60 or 70 degrees, with a fluorescein monomer incorporated near the end of the polymerization. The polymers were characterized via both proton NMR and GPC.

In various embodiments, unreacted succinimide groups can further be converted to non-bioactive groups to reduce in vivo side reactions.

In Scheme 8, a folic acid targeting agent is attached to the succinimide functional group.

Scheme 8

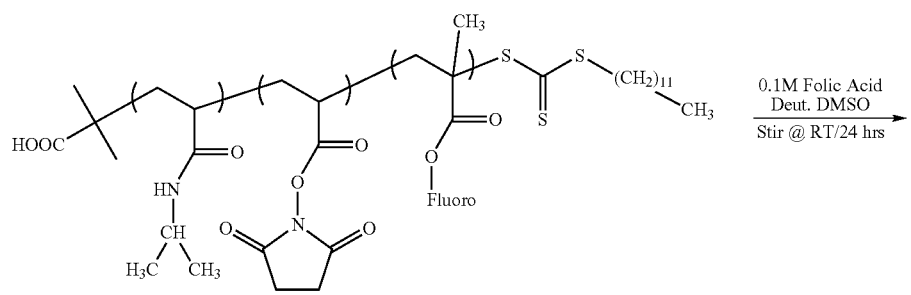

-continued

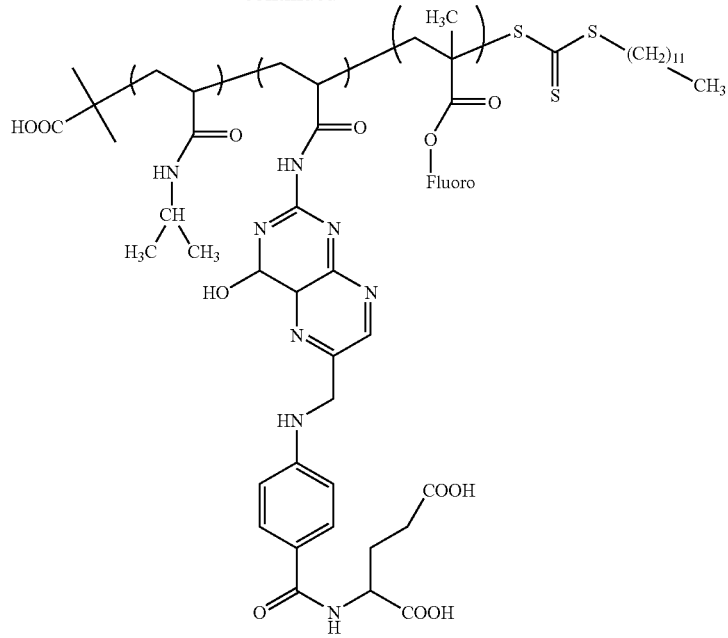

Figure 1B:
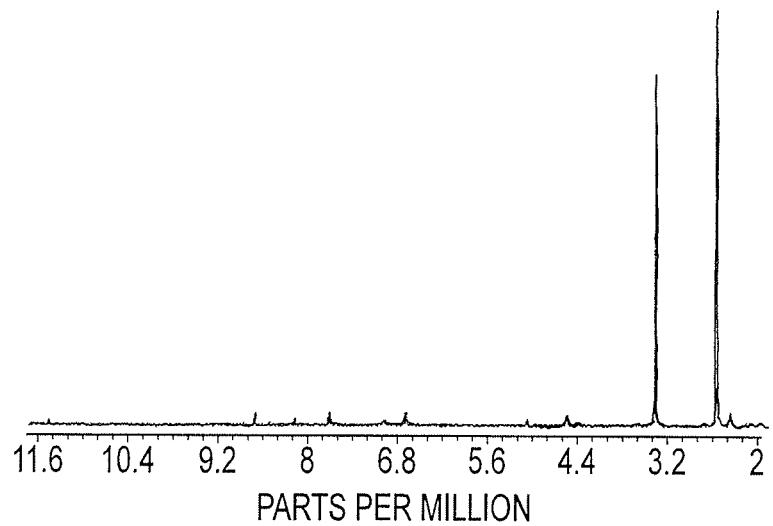
FIG. 1b depicts a ¹H NMR spectrum of folic acid.
Figure 1C:
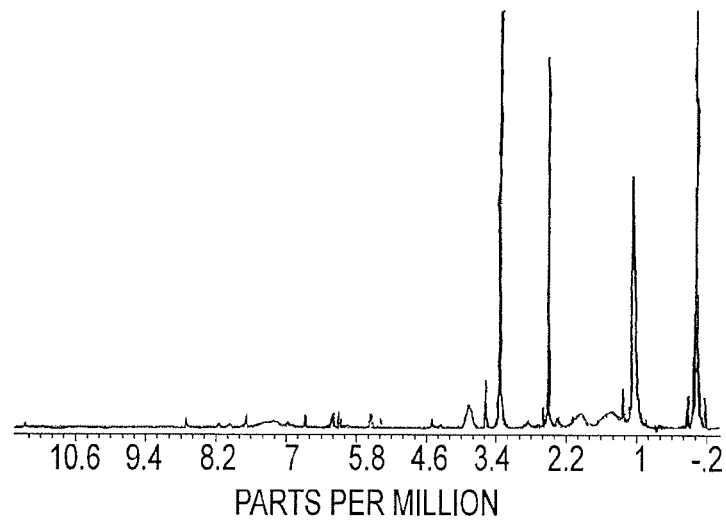
FIG. 1c depicts a ¹H NMR spectrum of PNIPAM-co-PNAOS-co-PFMA copolymer reacted with folic acid.

FIG. 1a depicts a $^1$H NMR spectrum of PNIPAM-co-PNAOS-co-PFMA copolymer. FIG. 1b depicts a $^1$H NMR spectra of folic acid. FIG. 1c depicts a $^1$H NMR spectrum of PNIPAM copolymer reacted with folic acid.

Other Methods

Aside from the in vivo diagnosis and treatment of cancer, with attachment of appropriate therapeutics and/or targeting moieties, the invention may be used for a wide variety of different drug delivery applications, such as gene therapy, imaging applications, such as vascular imaging, and even in external molecular detection devices, such as microarrays and assays. The primary industry interested in the invention would be pharmaceutical companies. While these applications have been mentioned specifically there may be many more applications that the inventors have not considered or are yet to be thought of for the invention.

EXAMPLES

The following examples are intended to be exemplary, and not limit, the present disclosure.

Example 1

Figure 4A:
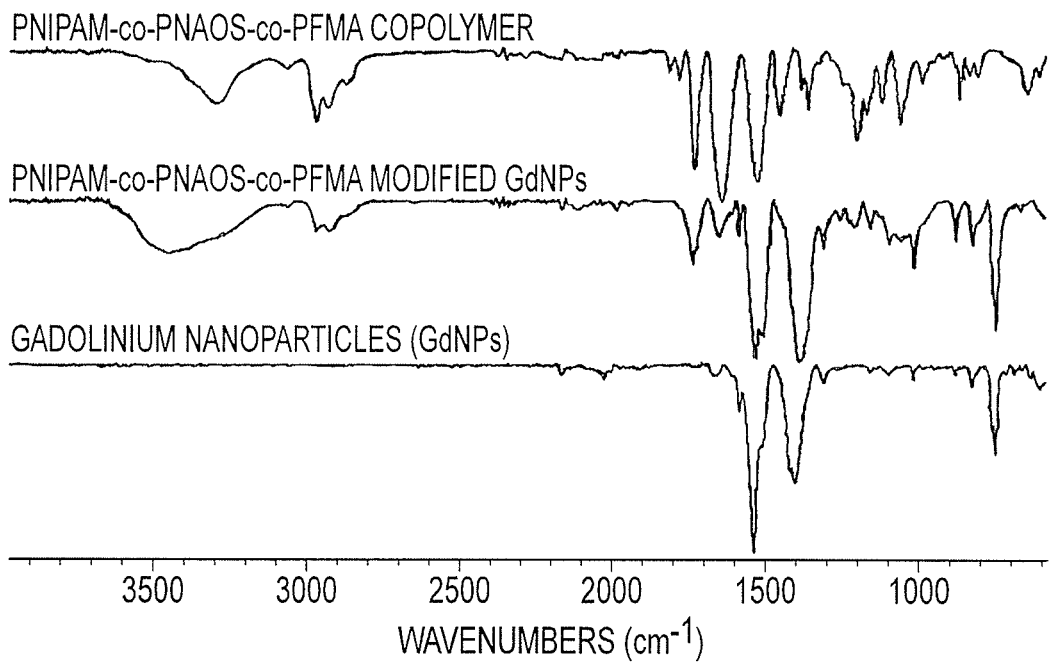
FIGS. 4(a-c) depict the Attenuated Total Reflection Fourier Transform Infrared (ATR-FTIR) spectra of gadolinium nanoparticles modified with (a) PNIPAM-co-PNAOS(@25% wt), (b) PDMAEA-co-PNAOS(@25% wt)-co-PFMA, and (c) PPEGMEA-co-PNAOS(@25% wt)-co-PFMA copolymers.
Figure 4B:
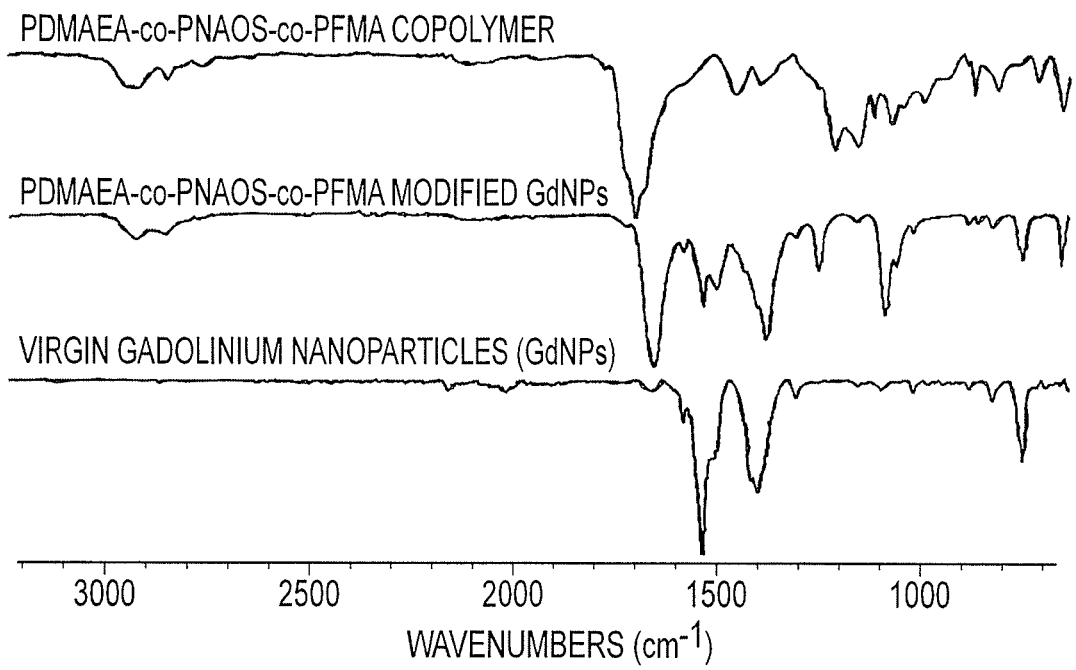
Figure 4C:
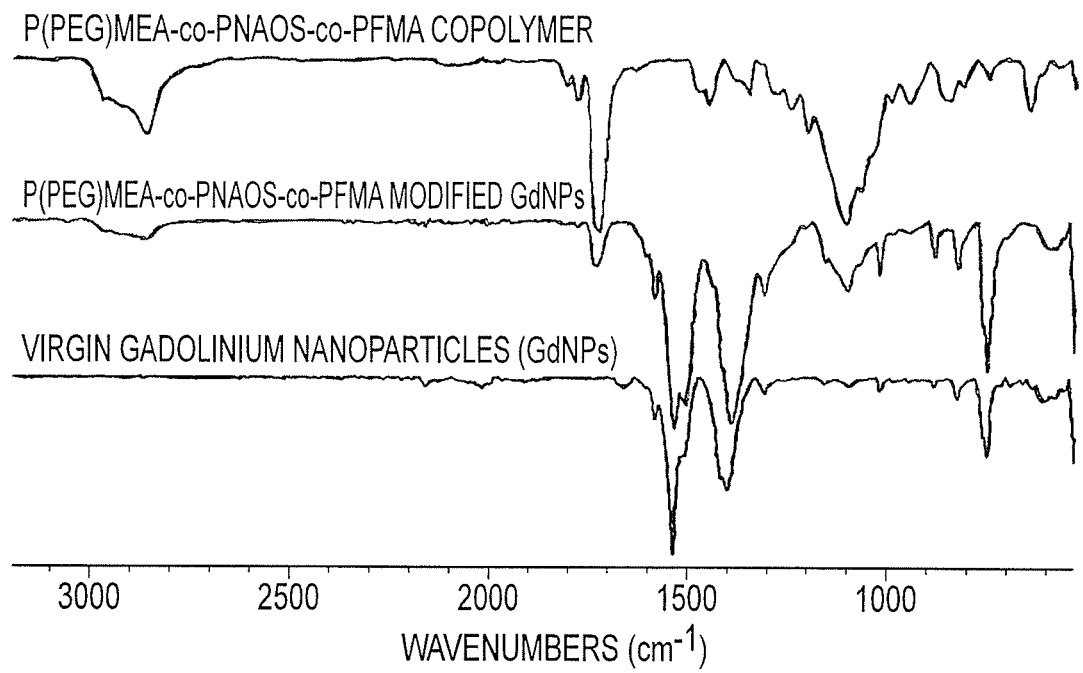

To gain more concrete evidence of the presence of polymer on the Gd nanostructures, surface modification of the Gd nanoparticles with RAFT polymers was characterized through both TEM and ATR-FTIR both before and after coating with the RAFT polymer. FIG. 4 depicts the ATR-FTIR spectra of gadolinium nanoparticles modified with (a) PNIPAM-co-PNAOS(@25% wt), (b) PDMAEA-co-PNAOS (@25% wt)-co-PFMA, and (c) PPEGMEA-co-PNAOS (@25% wt)-co-PFMA copolymers. The top spectrum in each of a), b) and c) is that of the free copolymer, the second spectrum is that of the uncoated nanostructures, and the third spectrum is that of the coated gadolinium nanoparticles. As can be clearly seen after coating of the nanoparticles and extensive washing procedures, peaks from the amine and the carbonyl of the copolymer appear in the spectra of the particles. This suggests that the nanostructures are coated with the copolymer.

Figures 3A, 3B, 3C:
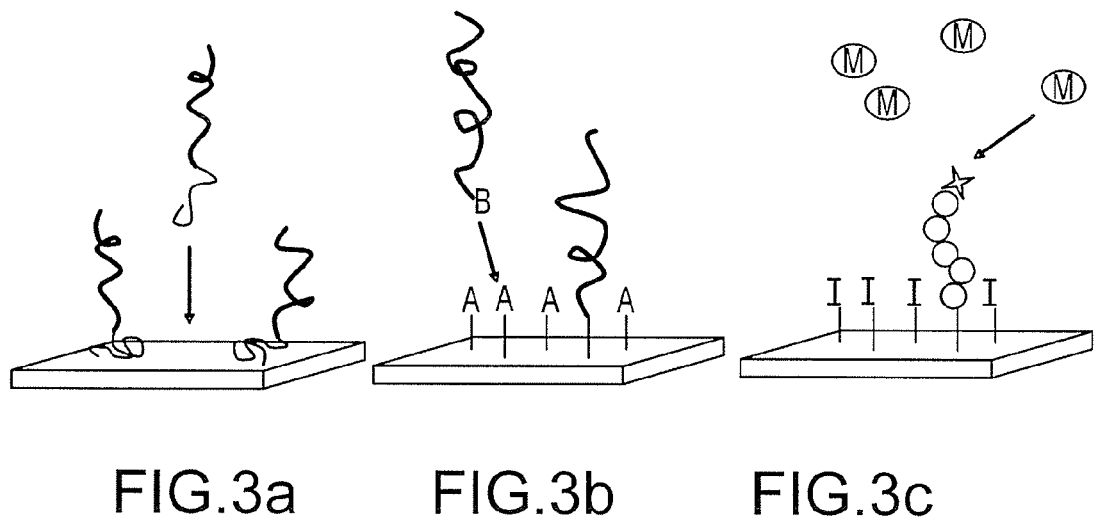
FIGS. 3(a-c) depict preparations of polymer modified surfaces by the (a) physisorption, (b) 'grafting to', and (c) 'grafting from' methods.
FIG. 3d depicts a proposed coordination mechanism attachment of thiolate polymer chain ends to MOFs of Gd nanoparticles (NPs) synthesized by a reverse microemulsion system employing the 1,4-BDC ligand.
Figure 3D:
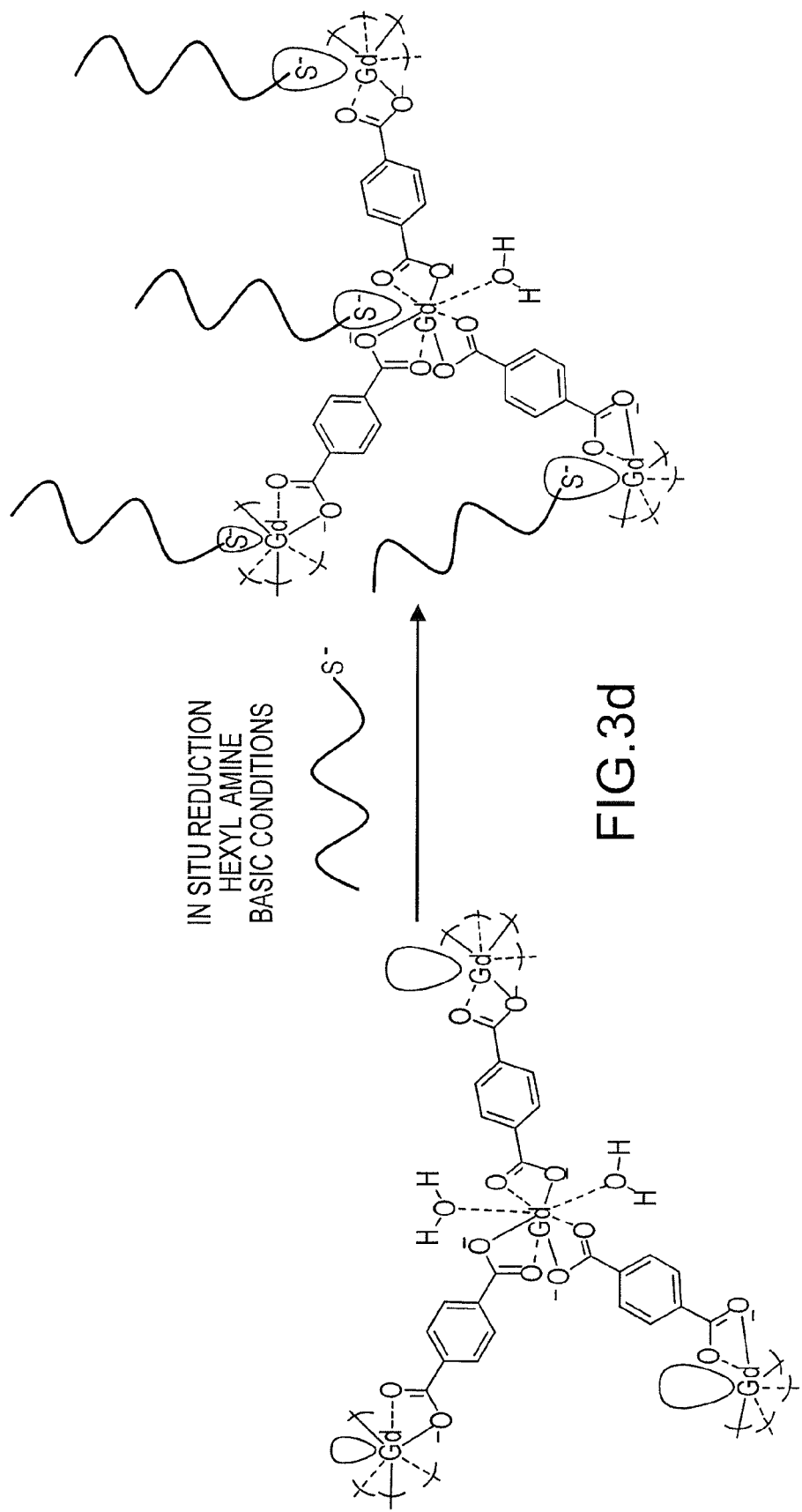
Figure 15A:
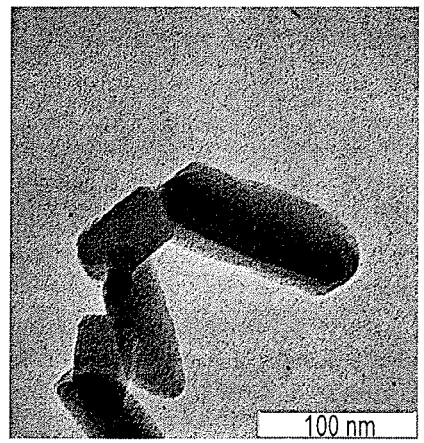
FIG. 15(a-c) depict TEM images of Gd NPs modified with (a) PNIPAM, (b) PDMAEA, and (c) PPEGMEA homopolymers synthesized by RAFT polymerization.
Figure 15B:
Figure 15C:
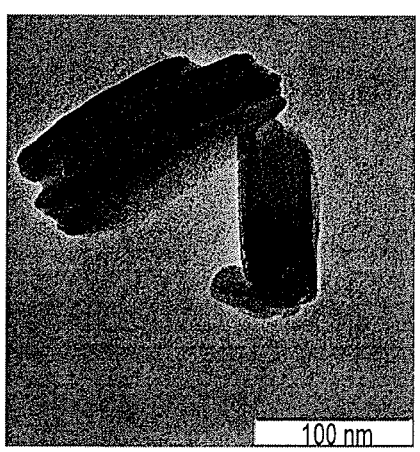

The TEM images (FIG. 15) indicate a uniform coating of the each of the RAFT polymers around the Gd nanoparticles after deposition. This further confirms that the nanostructures are coated with the copolymer. The modification of Gd nanoparticles was achieved by an initial aminolysis, using hexylamine, of the trithiocarbonate or dithioester end group of the RAFT polymers to a thiolate functionality under inert and basic conditions. Without being limited to a specific mechanism or mode of action, one mechanism of attachment is shown in FIG. 3d, where the thiolate terminated polymer is covalently attached to the nanoparticle surface through a coordination reaction between the polymer chain thiolate end-group moiety and vacant orbitals on the $Gd^{3+}$ ions at the surface of the Gd nanoparticles.

Example 2

Figure 17A:
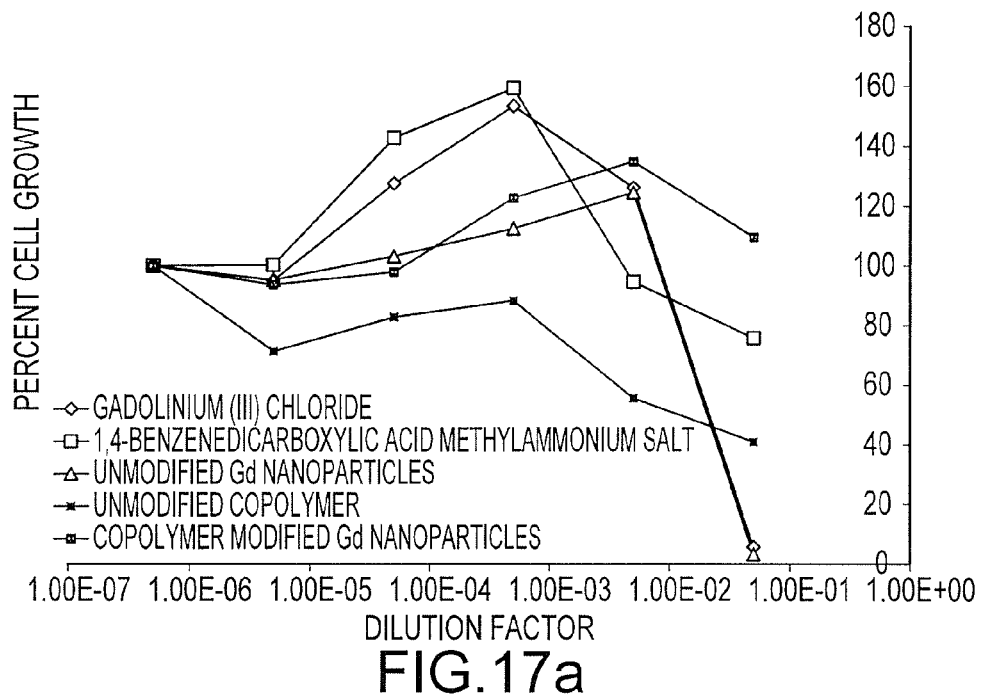
FIGS. 17(a-b) depict cell inhibition studies for (a) reagents involved in nanomedicine formation, including gadolinium (III) chloride, 1,4-benzenedicarboxylic acid methylammonium salt, unmodified Gd NPs, unmodified PNIPAM-co-PNAOS-co-PFMA, and PNIPAM-co-PNAOS-co-PFMA modified Gd NPs and (b) multifunctional nanovectors including MTX drug, PNIPAM-co-PNAOS-co-PFMA tailored with MTX, Gd NPs modified with PNIPAM-co-PNAOS-co-PFMA tailored with MTX, and Gd NPs modified with PNIPAM-co-PNAOS-co-PFMA tailored with both MTX and RGD.

The ability of the nanoparticles to inhibit in vitro cell growth was measured. The reagents for nanodevice formation, i.e. $GdCl_3$ salt, 1,4-benzenedicarboxylic acid methylammonium salt, unmodified Gd nanoparticles, and Gd nanoparticles modified with RAFT copolymers were studied (FIG. 17a). The increased cell viability is attributed to coating of the Gd nanoparticles with copolymers consisting of the biocompatible polymer PNIPAM. This infers that the presence of the RAFT copolymer on the surface of the Gd nanoparticles increases the biocompatible nature of the nanodevice. Canine osteosarcoma cells were initially used as a proof of concept study and the systems were incubated at physiological temperature, 37° C. for 72 hours in a 5% $CO_2$ atmosphere. Preliminary growth inhibition curves for nanoparticles, unmodified polymers, and polymer modified nanoparticles confirm that none of the compounds show a significant anti-proliferative or cytotoxic effect on the incubated cancer cells.

A range of therapeutic agents and targeting agents were tested for efficacy following post-polymerization covalent attachment of the PNIPAM-co-PNAOS(@25% wt)-co-PFMA copolymer with the agents. Tested therapeutic agents included Paclitaxel and Methotrexate. Targeting agents include folic acid and GRGD sequences.

Samples were incubated with canine FITZ cells at physiological temperature for 4, 24, and 72 hours in a 5% $CO_2$ atmosphere. These cells lines chosen based on their susceptibility to the therapeutic agents being tested, along with targeting ability through the GRGD sequences.

Figure 17B:
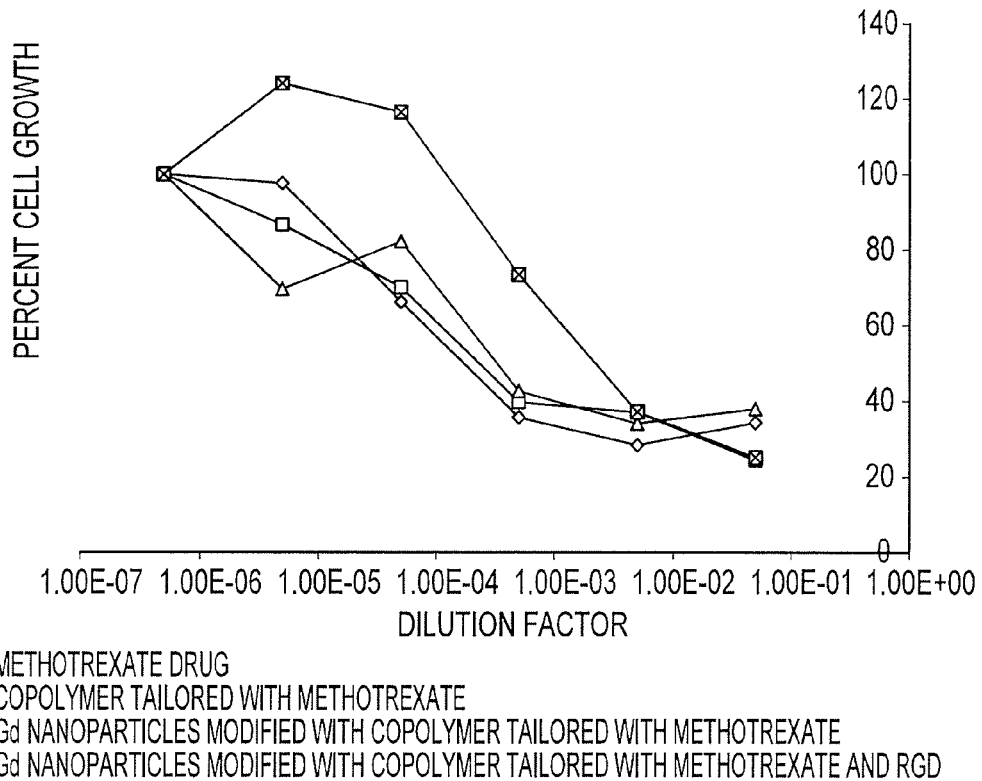

FIG. 17b depicts growth inhibition curves for gadolinium nanoparticles modified with PNIPAM-co-PNAOS(@25% wt)-co-PFMA incubated in FITZ cells. Growth inhibition curves for gadolinium nanoparticles modified with PNIPAM-co-PNAOS(@25% wt)-co-PFMA and Methotrexate show cell death at higher concentration of the drug within the FITZ cell line and follow similar growth inhibition activity in comparison to the free Methotrexate drug. The addition of RGD to the polymer modified gadolinium nanoparticle sample shows little to no effect on the therapeutic activity of the Methotrexate.

Figure 11:
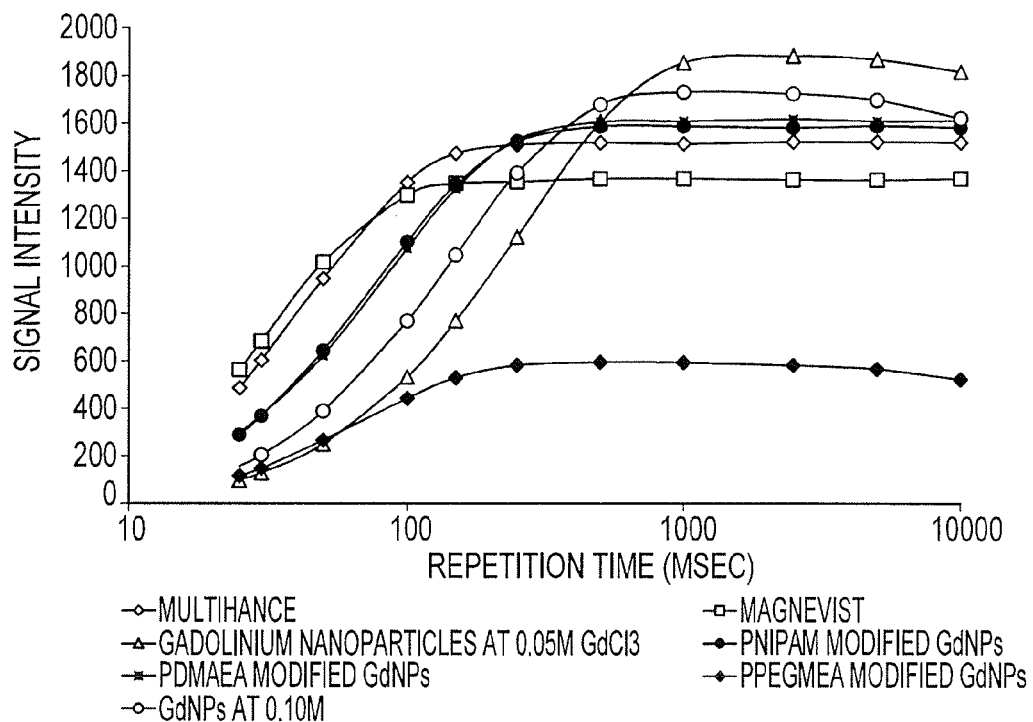
FIG. 11 depicts experimental T1 relaxation time curves for clinical MRI contrast agents, Multihance® and Magnevist® along with the unmodified and polymer modified Gd NPs.
Figure 12:
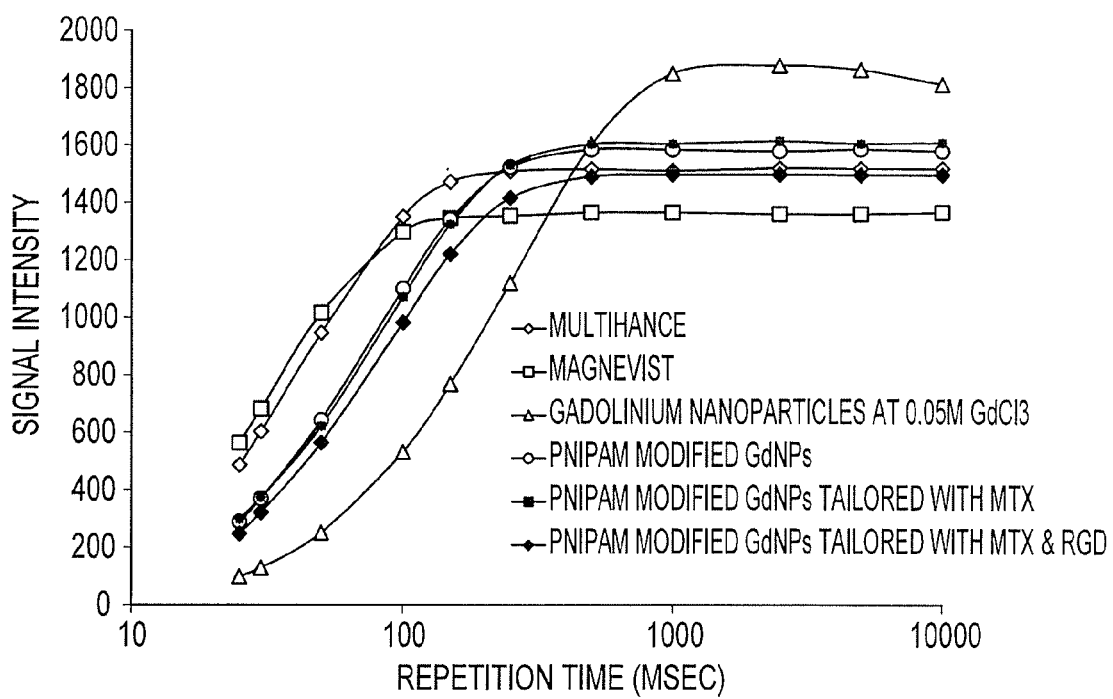
FIG. 12 depicts experimental T1 relaxation time curves for clinical MRI contrast agents, Multihance® and Magnevist® along with the unmodified and polymer modified Gd nanoparticle conjugates that include chemotherapeutic agents MTX and RGD.

MRI data is shown in FIGS. 11 and 12. FIG. 11 shows the MRI relaxation time data for Magnevist, Multihance, gadolinium nanoparticles synthesized at [$GdCl_3$] of 0.05M, gadolinium nanoparticles synthesized at [$GdCl_3$] of 0.10M, PNIPAM homopolymer modified gadolinium nanoparticles, PDMAEA homopolymer modified gadolinium nanoparticles, and PPEGMEA homopolymer modified gadolinium nanoparticles. Table 1 shows $Gd^{3+}$ concentrations and calculated T1 relaxation times for the various compounds. All samples were diluted with deionized ultra-filtered water and purged with high purity nitrogen before characterization. Sample data was collected at room temperature. Magnevist and Multihance are currently utilized MRI contrast agents on the clinical level and so were used as controls. The T1 relaxation curves (FIGS. 11 and 12) demonstrate that both the unmodified and polymer modified Gd NPs result in a large shortening of the T1 relaxation time and, thus, behave as positive contrast agents, similar to the results shown for the Magnevist and Multihance controls. Additionally, a significant increase in signal intensity with increased relaxation times in the gadolinium nanoparticles synthesized at [$GdCl_3$] of 0.10 M in comparison to the gadolinium nanoparticles synthesized at [$GdCl_3$] of 0.05M. This data suggests that relaxation time properties can be changed with changing the gadolinium (III) chloride incorporated within the microemulsion systems. It is also important to note the relativity of the gadolinium nanoparticles is not affected with modification with the polymeric scaffolds to form gadolinium nanoparticle conjugates to be used as a MRI contrast agents. The bottom graph shows the MRI relaxation time data for Magnevist, Multihance, gadolinium nanoparticles synthesized at [$GdCl_3$] of 0.05M, PNIPAM copolymer modified gadolinium nanoparticles tailored with Methotrexate, and PNIPAM copolymer modified gadolinium nanoparticles tailored with both Methotrexate and $GRGD-NH_2$.

TABLE 1

[$Gd^{3+}$] values and T1 relaxation times for clinical MRI contrast agents, Multihance ® and Magnevist ®, along with the unmodified and polymer modified Gd NPs.

| Contrast Agent | [$Gd^{3+}$], mmol/L$^a$ | T1 Data (msec) |
|---|---|---|
| Magnevist | $3.10 \times 10^{-3}$ | 54 |
| Multihance | $3.10 \times 10^{-3}$ | 41 |
| Gd NPs at 0.05M GdCl3 | $1.16 \times 10^{-3}$ | 298 |
| Gd NPs at 0.10M GdCl3 | $1.63 \times 10^{-3}$ | 183 |
| PNIPAM Modified Gd NPs | $1.00 \times 10^{-3}$ | 99 |
| PDMAEA Modified Gd NPs | $1.03 \times 10^{-3}$ | 93 |

TABLE 1-continued

[$Gd^{3+}$] values and T1 relaxation times for clinical MRI contrast agents, Multihance ® and Magnevist ®, along with the unmodified and polymer modified Gd NPs.

| Contrast Agent | [$Gd^{3+}$], mmol/L$^a$ | T1 Data (msec) |
|---|---|---|
| PPEGMEA Modified Gd NPs | $1.08 \times 10^{-3}$ | 80 |
| Magnevist | $3.10 \times 10^{-3}$ | 54 |
| Multihance | $3.10 \times 10^{-3}$ | 41 |
| Gd NPs at 0.05M GdCl3 | $1.16 \times 10^{-3}$ | 298 |
| PNIPAM-co-PNAOS-co-PFMA Modified Gd NPs | $2.03 \times 10^{-3}$ | 94 |
| MTX Tailored RAFT Copolymer Modified Gd NPS$^b$ | $2.94 \times 10^{-3}$ | 99 |
| MTX/RGD Tailored RAFT Copolymer Modified Gd NPs$^{b,c}$ | $2.02 \times 10^{-3}$ | 103 |

$^a$[$Gd^{3+}$] determined by inductively coupled plasmon-absorption emission spectroscopy.

Figure 5A:
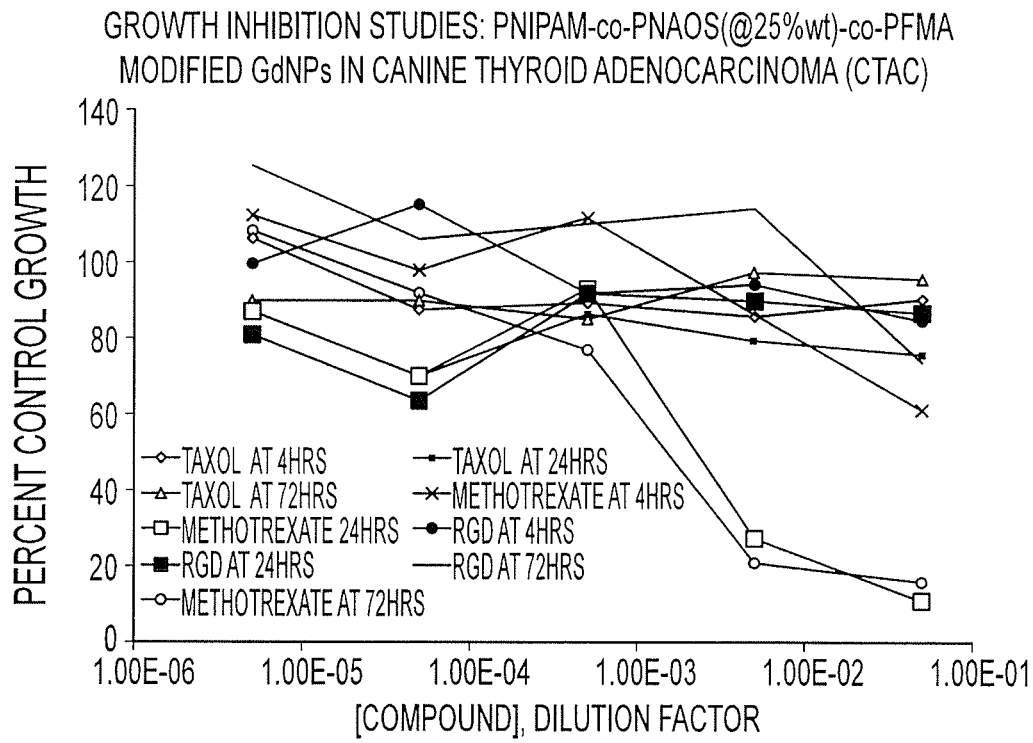
FIGS. 5(a-b) depict growth inhibition curves for gadolinium nanoparticles modified with PNIPAM-co-PNAOS (@25% wt)-co-PFMA containing either a cancer chemotherapeutic or targeting ligand incubated in (a) canine thyroid adenocarcinoma (CTAC) and (b) canine endothelial hemangiosarcoma (FITZ).
Figure 5B:
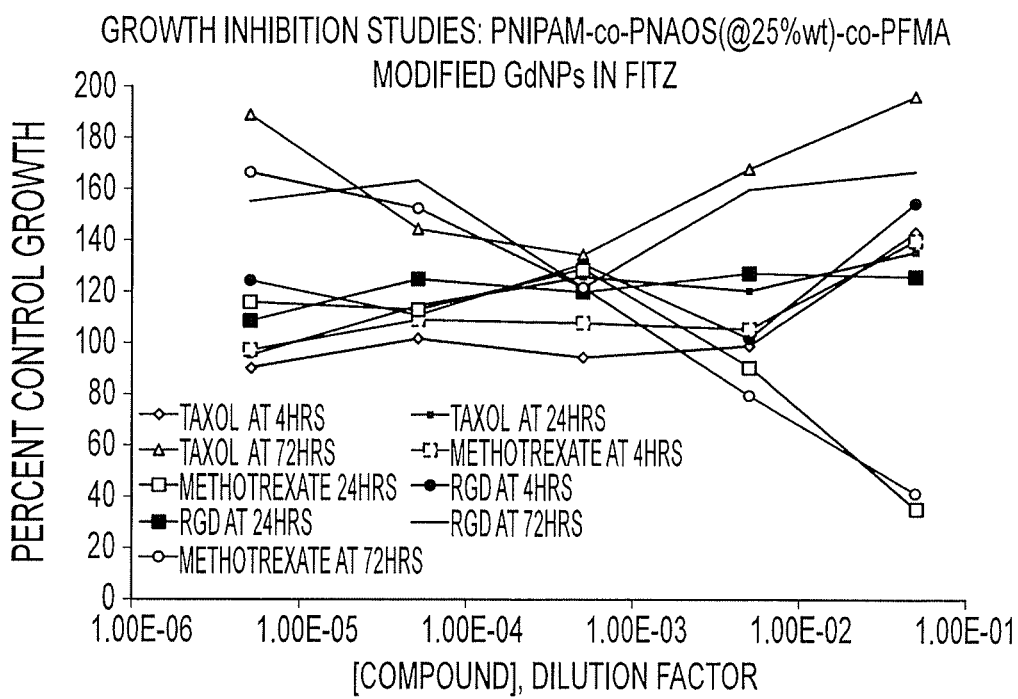
Figure 6:
FIG. 6 depicts MRI images of (a) Magnevist, (b) Multihance, (c) virgin gadolinium nanoparticles, (d) gadolinium nanoparticles modified with PNIPAM-co-PNAOS(@25% wt)-co-PFMA, and (e) gadolinium nanoparticles modified with PNIPAM-co-PNAOS(@25% wt)-co-PFMA and folic acid.

FIG. 5 depicts a growth inhibition curves for gadolinium nanoparticles modified with PNIPAM-co-PNAOS(@25% wt)-co-PFMA incubated in (a) CTAC and (b) FITZ. Growth inhibition curves for gadolinium nanoparticles modified with PNIPAM-co-PNAOS(@25% wt)-co-PFMA and Methotrexate show cell death at higher concentration of the drug within both the CTAC and FITZ cell lines. As expected the RGD sample shows little to no effect on cell death due to the lack of therapeutic agent. The Paclitaxel (Taxol) sample showed minimal cell death in the initial studies, which was attributed to a much smaller concentration of the drug, Taxol, in comparison to the Methotrexate sample.

Example 3

FIG. 7a-d depicts images of PNIPAM copolymer modified gadolinium nanoparticles tailored with Methotrexate and GRGD-NH2 (FIG. 7a-b) along with the PNIPAM copolymer modified gadolinium nanoparticles tailored with only Methotrexate (FIG. 7c-d), through fluorescence microscopy using a canine endothelial hemangiosarcoma (FITZ). (FITZ expresses the α,β-integrin used in these studies for biomolecular recognition.)

Figure 7:
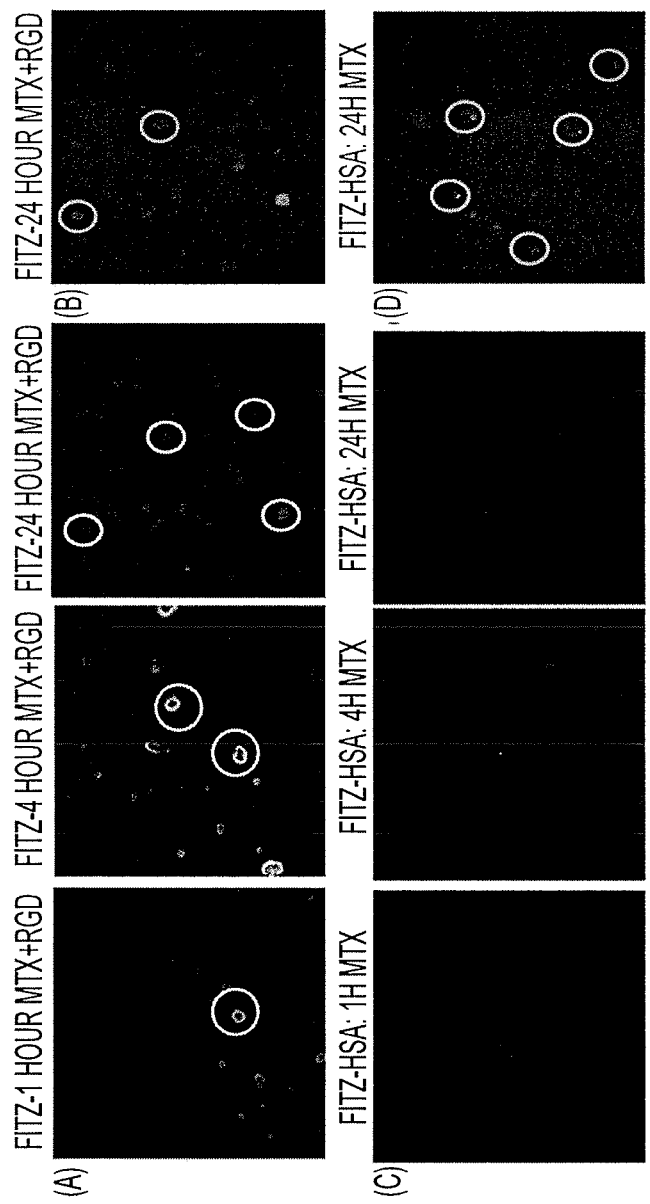
FIG. 7 depicts fluorescence and Texas Red microscopy images of targeted and non-targeted Gd NPs. (a) Fluorescence microscopy image of FITZ-HSA cells incubated with Methotrexate (MTX)/GRGD tailored copolymer modified Gd nanoparticles at 1, 4, and 24 h and corresponding microscopy image (b) of FITZ-HSA cells stained with propidium iodide for the 24 h study. (c) Fluorescence microscopy image of FITZ-HSA cells incubated with the control system of MTX tailored copolymer modified Gd NPs at 1, 4, and 24 h and corresponding microscopy image (d) of FITZ-HSA cells stained with propidium iodide for the 24 h study.
Figure 8:
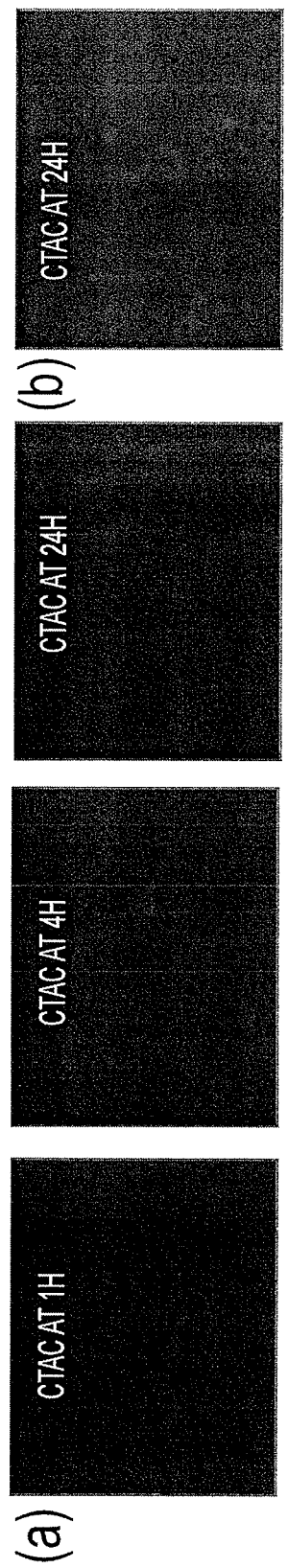
FIG. 8 depicts fluorescence and Texas Red microscopy images of targeted and non-targeted Gd NPs. (a) Fluorescence microscopy image of CTAC cells incubated with MTX/GRGD tailored copolymer modified Gd NPs at 1, 4, and 24 h and corresponding microscopy image (b) of CTAC cells stained with propidium iodide for the 24 h study.
Figure 9:
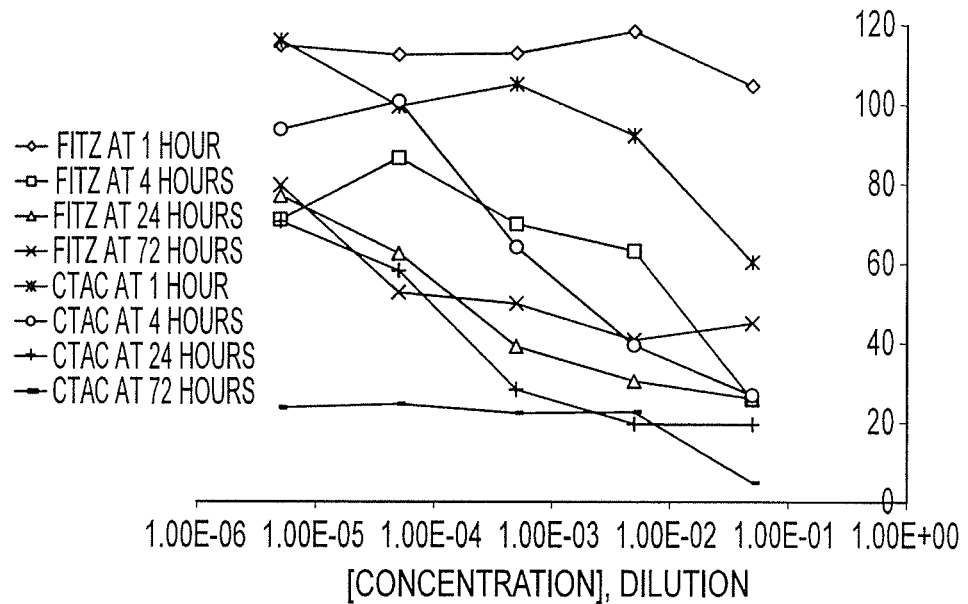
FIG. 9 depicts the cell viability studies with PNIPAM copolymer modified gadolinium nanoparticles tailored with Methotrexate.
Figure 10:
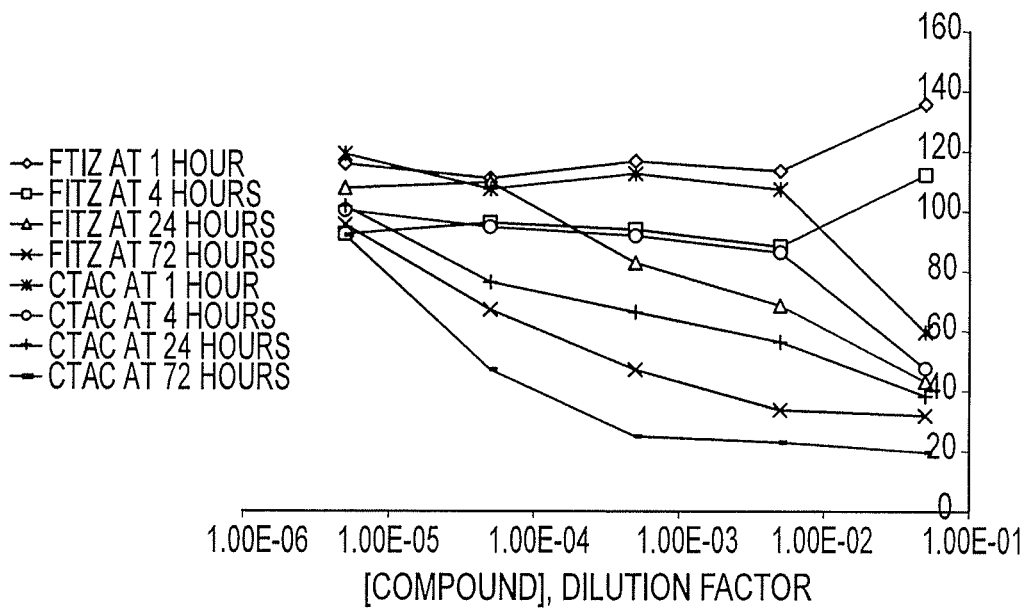
FIG. 10 depicts the cell viability studies with PNIPAM copolymer modified gadolinium nanoparticles tailored with Methotrexate and GRGD-NH₂.

Preliminary targeted, fluorescence cell imaging is shown in FIGS. 7 and 8. The targeted, imaging studies involved two cancer cell lines, CTAC (FIG. 8a-d) and FITZ (FIG. 7a-d), in which CTAC does not show the α,β-integrin and FITZ does express the α,β-integrin. Utilization of these two different cell lines provides a means of demonstrating tumor targeting through biomolecular recognition through the $GRGD-NH_2$ ligand. The samples in this study involved gadolinium nanoparticles modified with our PNIPAM copolymer. The PNIPAM construct is copolymerized with fluorescein O-methacrylate, which allows fluorescence imaging of the modified nanoparticles. The PNIPAM copolymer was then tailored with (Methotrexate) MTX and the targeting ligand, $GRGD-NH_2$ or only MTX. In FIG. 7a, after one hour we see little to no fluorescence signal. After just 4 hours, FIG. 7a demonstrates a 'haloing effect' on the periphery of the cells, what seems to be the targeted nanoparticles to be attaching to the exterior of the cells attributed to over expression of α,β-integrin. Additionally, the internalization of the multifunctional platform has occurred after 24 hours. This is demonstrated by imaging of the cells with a Texas Red dye, FIG. 7b, mirrored by fluorescence imaging of the cell enveloped nanoparticles in FIG. 7a. The combination of these images shows the promise of our nanoparticles to provide an imaging capable, tumor targeting device.

Additionally a control imaging system was run with a non-α,β-integrin showing cell line, CTAC, shown in FIGS.

8a-b, which depicts the images of PNIPAM copolymer modified gadolinium nanoparticles tailored with Methotrexate, through fluorescence microscopy using canine thyroid adenocarcinoma (CTAC). (CTAC does not express the α,β-integrin used in these studies for biomolecular recognition.)

As can be seen by all of these fluorescence images, along with the Texas Red image, there appears to be no targeting of the CTAC cells with the multifunctional systems.

Example 4

A range of stability tests were undertaken in an attempt to digest the Gd NPs. Basic, acidic, reducing, oxidizing, ferric, and physiological aqueous conditions were utilized: sodium hydroxide (12.01 g), Gd NPs (0.0123 g), DIUF water (20 mL), 100° C., 48 h; concentrated nitric acid (20 mL), Gd NPs (0.0114 g), 100° C., 48 h; concentrated sulfuric acid (20 mL), Gd NPs (0.0121 g), 100° C., 48 h; aqua regia (25 mL), Gd NPs (0.0112 g), 100° C., 48 h; sodium borohydride (0.0555 g), Gd NPs (0.0132 g), DIUF water (20 mL), 100° C., 48 h; iron (III) nitrate (0.0207 g), Gd NPs (0.0122 g), DIUF water (20 mL), 100° C., 48 h; potassium ferricyanide (0.1675 g), Gd NPs (0.0110 g), DIUF water (20 mL), 100° C., 48 h; and 0.9% saline isotonic sodium chloride solution (20 mL), Gd NPs (0.0142 g), 37° C., 48 h.

In each case, an aliquot of the Gd NP solution was taken for ICP-AES analysis in order to determine the initial [$Gd^{3+}$]. The Gd NPs were the introduced to a specific environment and stirred for 48 h at 100° C., with the exception of the physiological samples which were run for 48 h at 37° C. After the attempted digestion, the Gd NPs were cleaned through multiple centrifugation steps in DIUF water in order to remove any excess digestion reagents or leached $Gd^{3+}$. After each centrifugation step, the supernatants were combined and the Gd NPs were resuspended in DIUF water. The [$Gd^{3+}$] leached was then characterized by ICP-AES by characterization of both the Gd NPs and the supernatant.

The 0.9% saline solution at 37° C. has been shown in literature as a system that mimics physiological conditions. The leached $Gd^{3+}$ was then determined by ICP-AES (Table 5.3). In each case, over a 48 h time periods, there was minimal $Gd^{3+}$ leached from the Gd NPs, ranging between $7.63 \times 10^{-6}$ mmol/L and $4.36 \times 10^{-3}$ mmol/L, with the highest concentration being leached under extremely acidic conditions of the aqua regia. Additionally, a few example TEM images showed that the Gd NPs after each digestion were comparable to their initial samples.

TABLE 2

Concentration of 'free' $Gd^{3+}$ leached during digestion studies determined by ICP-AES.

| Digestion Reagent | Condition | Released [$Gd^{3+}$] (mmol/L)[c] |
|---|---|---|
| Concentrated nitric acid[a] | Acidic | $4.20 \times 10^{-3}$ |
| Concentrated sulfuric acid[a] | Acidic | $4.26 \times 10^{-3}$ |
| Aqua regia[a] | Acidic | $4.26 \times 10^{-3}$ |
| 11M Potassium hydroxide[a] | Basic | $8.90 \times 10^{-5}$ |
| 0.075M Sodium borohydride[a] | Reducing | $7.63 \times 10^{-6}$ |
| 0.025M Potassium ferricyanide[a] | Oxidizing | $1.46 \times 10^{-5}$ |
| 0.0025M Iron nitrate[a] | Transmetalation | $8.52 \times 10^{-3}$ |
| 0.09% Isotonic saline solution[b] | Mimics physiological | $4.01 \times 10^{-4}$ |

[a]Digestions were run at 100° C.
[b]Digestions were run at 37° C.
[c][$Gd^{3+}$] were determined by ICP-AES.

Figure 16:
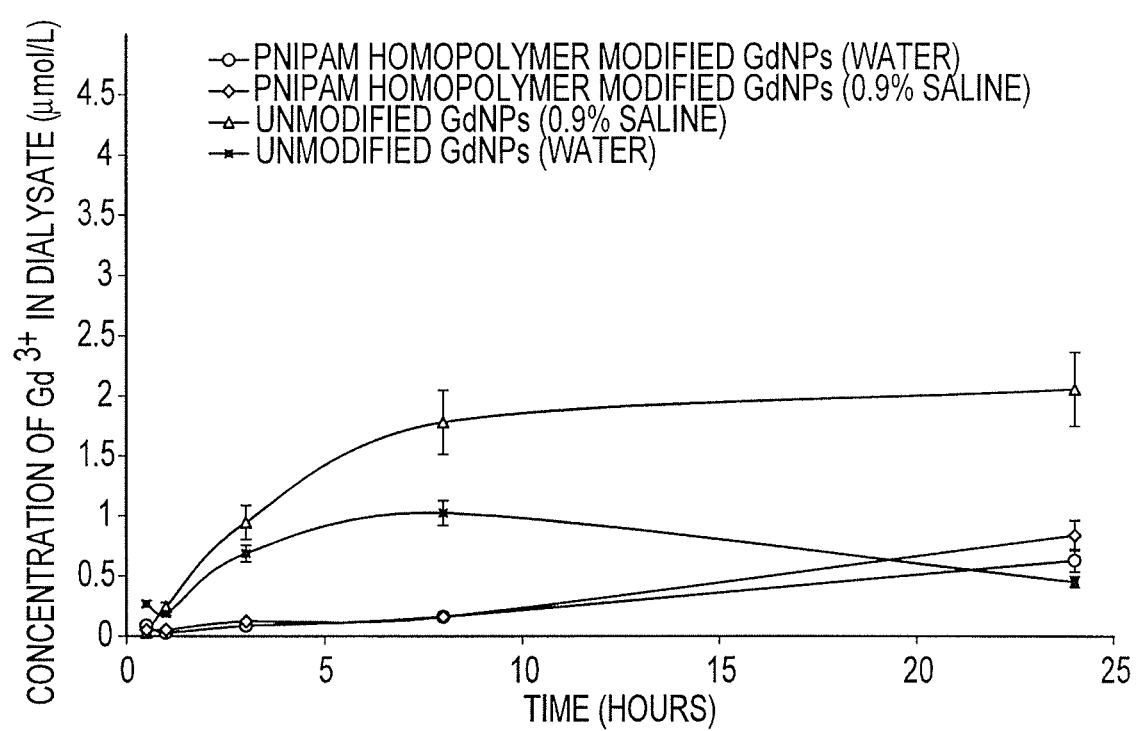
FIG. 16 depicts the concentration of 'free' $Gd^{3+}$ leached from unmodified and PNIPAM homopolymer modified Gd NPs during dialysis purification graphed as a function of time determine by inductively coupled plasmon-absorption emission spectroscopy.

As can be seen in FIG. 16 and Table 2, the purification of the Gd NPs by dialysis against DIUF water showed negligible leaching after 24 h with a maximum loss of 'free' $Gd^{3+}$ being 1.02 μmol/L, which is lower than that reported for a similar set of experiments discussed in the literature. Where the Gd NPs were dialyzed against the saline solution, which models a physiological environment, there was a negligible concentration of 'free' $Gd^{3+}$ seen in the dialysate, where the highest concentration was 2.05 μmol/L, further confirming the stability of the nanoscale MOF structure of the Gd NPs.

Additionally, in order to confirm that the gadolinium nanoparticle conjugates containing a PNIPAM homopolymer modification did not change the stability of the structures, dialysis purification was repeated following the same procedure as described for the unmodified Gd NPs. Again, ICP-AES was utilized and as can be seen in FIG. 16 there was only small concentration of 'free' $Gd^{3+}$ released from the polymer modified Gd NPs in either of the water or saline purified systems. Here the maximum $Gd^{3+}$ leached for the water dialysis experiment was 0.629 μmol/L and 0.837 μmol/L for the saline solution experiment.

These results demonstrate that gadolinium nanoparticle conjugates containing PNIPAM homopolymer leached half of the 'free' $Gd^{3+}$ in comparison to the unmodified Gd NPs and one-fourth that of the Gd NPs discussed in literature. These results suggest that the polymer modification of the Gd NPs provides a higher degree of stability to the Gd NPs. The results for the saline solution, which should mimic a physiological condition, dialysis study for the PNIPAM homopolymer modified Gd NPs further suggests their stability as a scaffold for Gd NP-based nanomedicines.

Applicants further note that the compounds and methods disclosed herein include those compounds cited in U.S. 2007/0123670 to McCormick et al., which is incorporated herein by reference in its entirety.

All references cited herein are incorporated herein by reference in their entirety.

We claim:

1. A gadolinium nanoparticle conjugate comprising:
Gd(1,4-benzenedicarboxylate)$_{1.5}$(H$_2$O)$_2$ directly grafted onto a polymer, polymer precursor, or initiator by a covalent bond or non-covalent bond, the gadolinium nanoparticle conjugate having the structural formula I

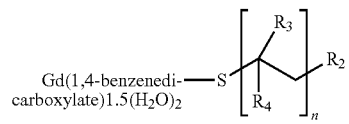

wherein n is an integer; and
$R_2$, $R_3$, and $R_4$ are each independently selected from the group consisting of hydrogen, alkyl, substituted alkyl, alkoxy, substituted alkoxy, acyl, substituted acyl, acylamino, substituted acylamino, alkylamino, substituted alkylamino, alkylsulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, aryloxycarbonyl, substituted aryloxycarbonyl, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy and substituted heteroaryloxy.

2. The gadolinium nanoparticle conjugate according to claim 1, further comprising a functional group not directly grafted onto said Gd(1,4-benzenedicarboxylate)$_{1.5}$(H$_2$O)$_2$.

3. The gadolinium nanoparticle conjugate according to claim 2, wherein the functional group not directly grafted onto said Gd(1,4-benzenedicarboxylate)$_{1.5}$(H$_2$O)$_2$ is selected from the group consisting of carboxylic acids, carboxylic acid salt derivatives, acid halides, sulfonic acids, sulfonic acid salts, anhydride derivatives, hydroxyl derivatives, amine derivatives, amide derivatives, silane derivatives, phosphate derivatives, nitro derivatives, succinimide derivatives, sulfo-containing succinimide derivatives, halide derivatives, alkene derivatives, morpholine derivatives, cyano derivatives, epoxide derivatives, ester derivatives, carbazole derivatives, azide derivatives, alkyne derivatives, acid containing sugar derivatives, glycerol analogue derivatives, maleimide derivatives, protected acids, protected alcohols, and acid halide derivatives.

4. The gadolinium nanoparticle conjugate according to claim 1, further comprising a therapeutic agent covalently bonded to said polymer.

5. The gadolinium nanoparticle conjugate according to claim 4, further comprising a targeting agent covalently bonded to said polymer.

6. A pharmaceutical composition comprising:
a gadolinium nanoparticle conjugate of claim 1, and
a pharmaceutically acceptable carrier.

7. A method of making a gadolinium nanoparticle conjugate comprising:
contacting a compound of Formula (III) or salt thereof with a compound of Formula (V) or a salt thereof to form the compound of Formula (VI):

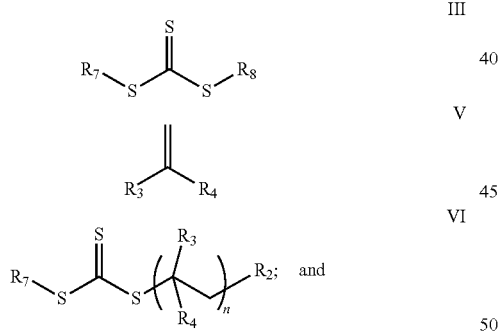

contacting the compound of Formula (VI) with Gd(1,4-benzenedicarboxylate)$_{1.5}$(H$_2$O)$_2$ to form a gadolinium nanoparticle conjugate having the structural formula I:

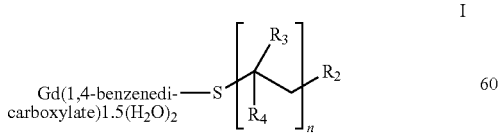

wherein n is an integer, and
R$_2$, R$_3$, R$_4$, R$_7$, and R$_8$ are each independently selected from the group consisting of hydrogen, alkyl, substituted alkyl, alkoxy, substituted alkoxy, acyl, substituted acyl, acylamino, substituted acylamino, alkylamino, substituted alkylamino, alkylsulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, aryloxycarbonyl, substituted aryloxycarbonyl, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy and substituted heteroaryloxy.

8. The method of claim 7, further comprising a step of contacting a reducing agent to the compound of formula (III) before contacting said Gd(1,4-benzenedicarboxylate)$_{1.5}$(H$_2$O)$_2$ with said compound of formula (VI).

9. A method of making a gadolinium nanoparticle conjugate comprising:
contacting a compound of Formula (II) or salt thereof with a compound of Formula (V) or a salt thereof to form the compound of Formula (VII):

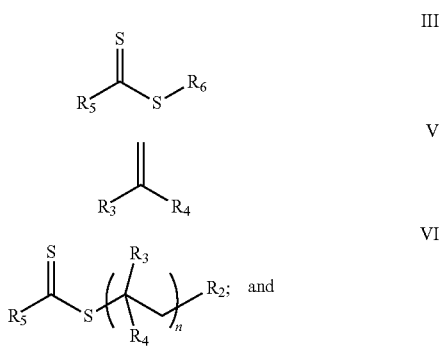

contacting the compound of Formula (VII) with Gd(1,4-benzenedicarboxylate)$_{1.5}$(H$_2$O)$_2$ to form a gadolinium nanoparticle conjugate having the structural formula I:

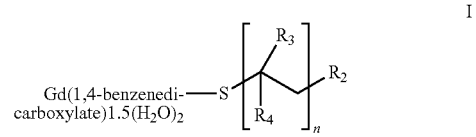

wherein n is an integer, and
R$_2$, R$_3$, R$_4$, R$_5$, and R$_6$ are each independently selected from the group consisting of hydrogen, alkyl, substituted alkyl, alkoxy, substituted alkoxy, acyl, substituted acyl, acylamino, substituted acylamino, alkylamino, substituted alkylamino, alkylsulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, aryloxycarbonyl, substituted aryloxycarbonyl, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy and substituted heteroaryloxy.

10. A method of treating a disease or disorder comprising: administering a gadolinium nanoparticle conjugate of claim 5 to a patient in need of treatment of said disease or disorder.

11. A method of treating a disease or disorder according to claim 10, further comprising obtaining an image of said gadolinium nanoparticle conjugate.

* * * * *